US 8,089,283 B2

(12) United States Patent
Kaplan et al.

(10) Patent No.: US 8,089,283 B2
(45) Date of Patent: Jan. 3, 2012

(54) APPARATUS AND METHOD FOR HIGH-SPEED DETERMINATION OF BIOELECTRIC ELECTRODE IMPEDANCES

(75) Inventors: Richard Kaplan, Richmond Heights, OH (US); Ying Wang, Richmond Heights, OH (US); Kenneth Loparo, Chesterland, OH (US)

(73) Assignee: Consolidate Research, Inc., Euclid, OH (US)

( * ) Notice: Subject to any disclaimer, the term of this patent is extended or adjusted under 35 U.S.C. 154(b) by 819 days.

(21) Appl. No.: 12/186,832

(22) Filed: Aug. 6, 2008

(65) Prior Publication Data

US 2009/0043221 A1 Feb. 12, 2009

Related U.S. Application Data

(60) Provisional application No. 60/955,157, filed on Aug. 10, 2007.

(51) Int. Cl.
*G01R 31/08* (2006.01)
*G01R 27/08* (2006.01)
*G01R 27/00* (2006.01)
*A61B 5/02* (2006.01)
*A61B 5/053* (2006.01)

(52) U.S. Cl. ........ 324/525; 324/691; 324/600; 600/506; 600/547

(58) Field of Classification Search .................. 324/525, 324/691, 600; 600/506, 547
See application file for complete search history.

(56) References Cited

U.S. PATENT DOCUMENTS

| | | |
|---|---|---|
| 3,381,088 A | 4/1968 | Lentz et al. |
| 3,699,947 A | 10/1972 | Maynard |
| 3,734,086 A | 5/1973 | Phelps, Sr. |
| 4,141,351 A | 2/1979 | James et al. |
| 4,245,643 A | 1/1981 | Benzing, III et al. |
| 4,428,380 A | 1/1984 | Wong et al. |
| 4,805,621 A | 2/1989 | Heinze et al. |
| 5,372,141 A | 12/1994 | Gallup et al. |
| 5,432,435 A | 7/1995 | Strong et al. |
| 5,755,742 A | 5/1998 | Schuelke et al. |
| 5,759,159 A | 6/1998 | Masreliez |
| 5,817,139 A | 10/1998 | Kasano |
| 5,921,939 A | 7/1999 | Danielsson et al. |
| 6,032,072 A | 2/2000 | Greenwald et al. |
| 6,292,690 B1 | 9/2001 | Petrucelli et al. |
| 6,472,888 B2 | 10/2002 | Oguma et al. |
| 6,625,487 B2 | 9/2003 | Herleikson |
| 6,760,624 B2 | 7/2004 | Anderson et al. |
| 6,882,166 B2 | 4/2005 | Shambroom et al. |
| 6,907,290 B2 | 6/2005 | Legay |
| 6,978,171 B2 | 12/2005 | Goetz et al. |
| 7,161,362 B2 | 1/2007 | Shambroom et al. |
| 7,245,961 B2 * | 7/2007 | Blakley et al. ............... 600/509 |
| 7,340,294 B2 * | 3/2008 | Gray ............................ 600/509 |
| 2002/0123773 A1 | 9/2002 | Molin |
| 2003/0006782 A1 | 1/2003 | Shambroom et al. |

(Continued)

*Primary Examiner* — Amy He
(74) *Attorney, Agent, or Firm* — Priya Sinha Cloutier

(57) ABSTRACT

Apparatuses and methods are provided for determining electrode impedances of a bioelectric signal-monitoring/recording system that includes an amplifier, and electrodes connected between a subject and the amplifier. An example apparatus includes: a voltage source outputting a voltage signal; a switching arrangement including an input electrically connected with the voltage source for receiving the voltage signal, an output electrically connected with the amplifier and the electrodes, and switches between the input and the output; and a controller in communication with the switches for opening and closing the switches to establish signal paths between the voltage source and the output, the controller calculating the electrode impedances relative to voltage outputs of the amplifier for each signal path.

37 Claims, 20 Drawing Sheets

U.S. PATENT DOCUMENTS

2003/0032989 A1 2/2003 Herleikson
2005/0001863 A1 1/2005 Farr et al.
2005/0101875 A1 5/2005 Semler et al.
2005/0203437 A1 9/2005 Shambroom et al.
2006/0020218 A1 1/2006 Freeman et al.

* cited by examiner

APPARATUS AND METHOD FOR HIGH-SPEED DETERMINATION OF BIOELECTRIC ELECTRODE IMPEDANCES

CROSS-REFERENCE TO RELATED PATENT APPLICATIONS

This patent application claims the benefit of U.S. Provisional Patent Application No. 60/955,157, filed Aug. 10, 2007.

FIELD OF THE INVENTION

This invention pertains generally to monitoring bioelectric signals, and more particularly to apparatuses and methods for high-speed determination of electrode impedances that exist during monitoring of bioelectric signals.

BACKGROUND OF THE INVENTION

To collect biological or bioelectric signals (e.g., electrocardiographic (ECG), electromyographic (EMG), electroencephalographic (EEG), etc.), it is often necessary to attach electrodes either on the surface of a subject's skin or implanted under the subject's skin. FIG. 1 illustrates an example block diagram of a conventional system that may be used for recording and analyzing EEG signals for the primary purpose of medical diagnostics. Power supplies, patient isolation, and many other elements of a complete bioelectric signal-monitoring system are not depicted in this example system since such features are well known to those versed in the art.

As shown in FIG. 1, the system 100 employs two signal electrodes 110, 120 and one common electrode 130 all of which are attached to a subject from whom it is desired to receive EEG signals. The electrodes 110, 120, 130 are placed at particular locations depending on the intended application. It is common in clinical and research applications to place several signal electrodes at various locations on the subject's head to obtain EEG information associated with different regions of the brain in either a differential arrangement, which is shown, or in a referential arrangement. Electrodes are typically secured to the subject's scalp to provide a stable mechanical connection therewith and, often, conductive gel or paste is used to establish a good electrical connection with relatively low impedance.

The body generates low voltage EEG electrical signals (in the microvolt range) with relatively high output impedance. To obtain sufficient amplitude for recording or processing, these EEG signals must be amplified. Accordingly, the electrodes 110, 120 are connected to an EEG amplifier 140. The common electrode 130 is used to ensure that the amplifier 140 and subject are at the same electrical potential. This can significantly reduce common mode interference and stabilize the amplification process. The electrodes 110, 120 are connected to the EEG amplifier 140 using suitable leads, which are selected to minimize noise contamination. Leads may be provided with a shield as an additional noise reduction step, but this can increase capacitance and the loading effects must be carefully considered. The EEG amplifier 140 is typically a high-input-impedance linear amplifier having several user-selectable gain settings in the range of $10^3$-$10^5$. A variety of EEG amplifiers are commercially available in various configurations. For example, Grass Technologies of West Warwick, R.I. sells a variety of clinical and research EEG amplifiers and systems.

The EEG amplifier 140 amplifies the differential signal between electrodes 110, 120 and produces an output voltage, $V_{amp}$, which is then filtered by, for example, a low pass filter 150 as shown. Then, the filtered output voltage is digitized by, for example, an A/D converter 160. The filtered and digitized signal is then typically fed to a digital signal processor (DSP) 170, processor, computer, etc. for numerical computations, storage, display, etc.

As shown in FIG. 1, the impedances at the junction between the subject's skin and the contact surface of the electrodes (i.e., skin-to-electrode impedances that are referred to hereinafter as "electrode impedances") are indicated as $Z_1$, $Z_2$ and $Z_c$ for the two signal electrodes 110, 120 and the common electrode 130 respectively. The quality of the electrical connection between the body and the electrodes can have a significant impact on signal quality. That is, high electrode impedances and/or disparate electrode impedances can lead to poor signal quality. For good signal quality, the electrode impedances $Z_1$, $Z_2$ and $Z_c$ should be measured to ensure that they are balanced and within limits that are appropriate for the intended application.

Although various apparatuses, systems and methods exist for measuring electrode impedances, use of such conventional apparatuses, systems and methods is somewhat disadvantageous because they generally require manual intervention where the electrode leads are disconnected from the amplifier thereby interfering with the signal-monitoring/recording process. For example, the EZM® Electrode Impedance Meters from Grass Technologies of West Warwick, R.I. provide the ability to manually test applied electrodes at the subject site before connection to the recording instrumentation. However, if one or more electrodes were to experience a fault condition (e.g., by becoming partially or entirely disconnected from the subject) that goes unnoticed during monitoring/recording of bioelectric signals, the conventional apparatuses, systems and methods would not be able to detect and indicate the fault condition.

Furthermore, use of the conventional apparatuses, systems and methods is disadvantageous because they are unable to accurately measure impedances of a small number of electrodes individually. As known in the art, these conventional apparatuses, systems and methods either measure electrode impedances in a pair-wise manner, or measure a single electrode in series with the parallel combination of the remaining electrodes. With regard to conventional apparatuses, systems and methods using pair-wise measurements, these conventional apparatuses, systems and methods will just provide the impedance sum of each pair, not the individual impedance value of each of the electrodes. With regard to conventional apparatuses, systems and methods that measure a single electrode in series with the parallel combination of the remaining electrodes, it can be appreciated that these apparatuses, systems and methods assume a large array of electrodes which results in the parallel combination of electrode impedances of the remaining electrodes being very small in comparison to the electrode being measured so that the sum is dominated by the measurement electrode. With only a few (e.g., 2 or 3) electrodes in parallel, one cannot assume that these parallel electrodes have a very small impedance in comparison to the electrode impedance of the electrode being measured.

In view of the foregoing, apparatuses, systems and methods for determining electrode impedances, particularly at high speed and without having to disconnect the electrodes from an amplifier, would be an important improvement in the art. Additionally, apparatuses, systems and methods for determining electrode impedances of a small number of electrodes individually would be an important improvement in the art.

BRIEF SUMMARY OF THE INVENTION

In one aspect, an apparatus is provided for determining electrode impedances of a bioelectric signal-monitoring/recording system that includes an amplifier and electrodes connected between a subject and the amplifier. An embodiment of the apparatus includes: a voltage source outputting a voltage signal; a switching arrangement including an input electrically connected with the voltage source for receiving the voltage signal, an output electrically connected with the amplifier and the electrodes, and switches connected between the input and the output; and a controller in communication with the switches for opening and closing the switches to establish signal paths between the voltage source and the output, the controller calculating the electrode impedances relative to voltage outputs of the amplifier for each signal path. In another aspect, a bioelectric signal-monitoring/recording system is provided that includes the apparatus for determining electrode impedances. In yet another aspect, a method is provided for determining electrode impedances of a bioelectric signal-monitoring/recording system.

DETAILED DESCRIPTION OF THE EMBODIMENTS

Turning now to the Figures, methods and apparatuses for high-speed determination of electrode impedance are provided. Embodiments of the present apparatus and method may be used to determine electrical impedance using voltage and current levels that are appropriate for use on living organisms such as humans and animals. An embodiment of the apparatus can measure the impedance of three electrodes in approximately 0.6 seconds, with approximately 0.2 seconds of measurement time needed for each additional electrode that is measured. The present apparatus and method can be extended to any number of electrodes, whether using a fully differential or a referential electrode configuration.

Figure 1:
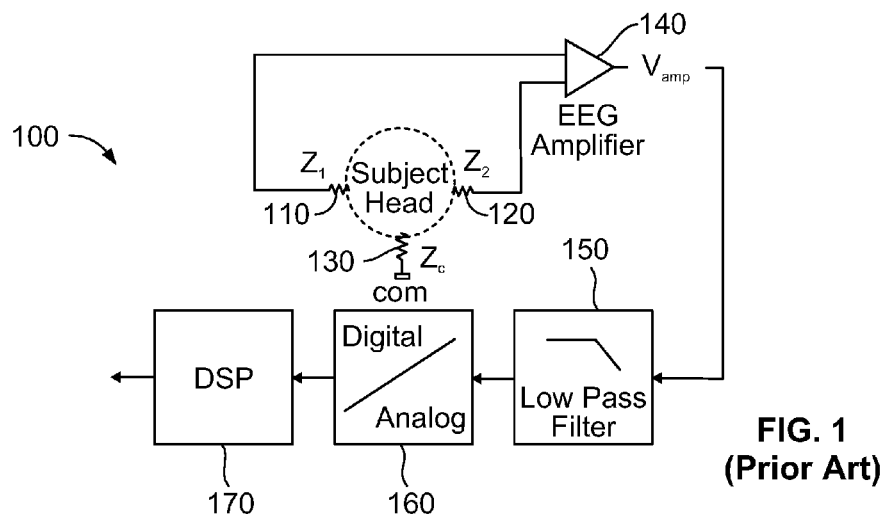
FIG. 1 illustrates a block diagram of a conventional system that may be used for recording and analyzing EEG signals for the primary purpose of medical diagnostics.

Various embodiments of apparatuses and methods according to the present invention can be added to existing hardware (e.g., a conventional bioelectric signal-monitoring/recording system such as the system shown in FIG. 1), integrated into new designs or configured as a stand-alone apparatus.

Theory of Operation

Figure 2:
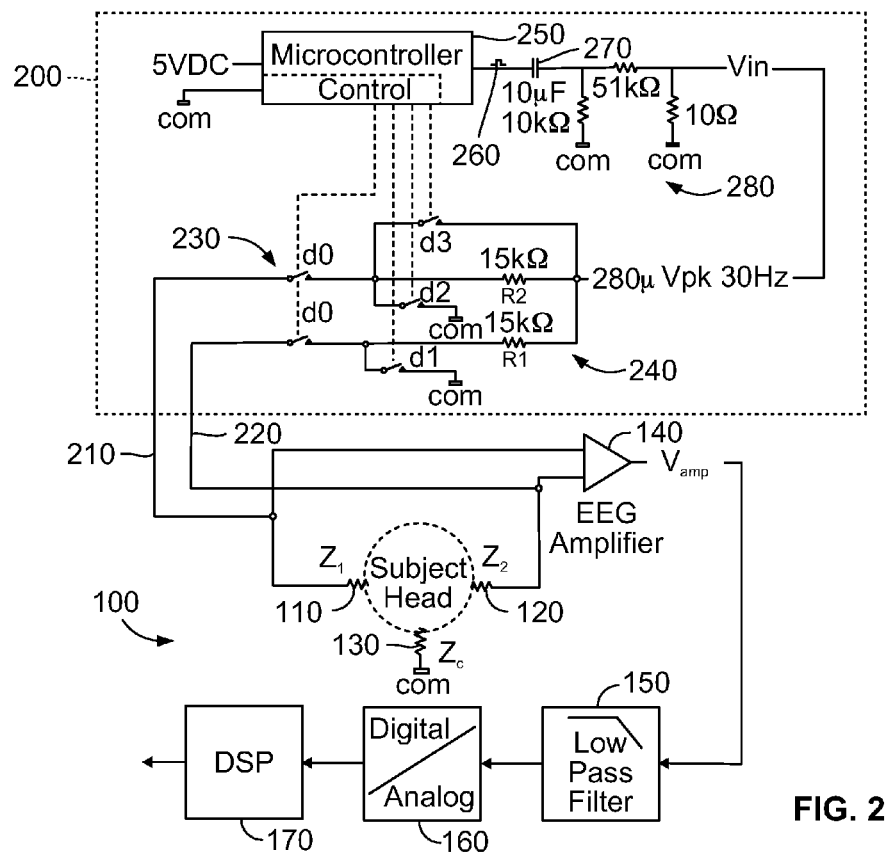
FIG. 2 illustrates a block diagram of an example apparatus according to an aspect of the present invention that may be employed with the system of FIG. 1 for high-speed determination of electrode impedances.

One embodiment of the present apparatus is shown in FIG. 2. The illustrated apparatus 200 could be made stand-alone or, alternatively, incorporated into a new or existing device or system (e.g., the system 100 of FIG. 1). Since many EEG systems, for example system 100 of FIG. 1, are already in use and include an EEG amplifier 140, A/D converter 160, etc., such systems may be equipped with impedance-determining capability by adding those components contained inside the dotted box, which may be relatively inexpensive. Although various component values are shown, the values should not be taken as being limiting on the present apparatus and method since the values are merely provided as examples for convenience of explanation. Furthermore, although the present apparatus and method are described in the context of use with EEG-monitoring systems, it should be appreciated that the present apparatus and system may be used with other biological/bioelectric signal-monitoring/recording systems as well.

Figure 3:
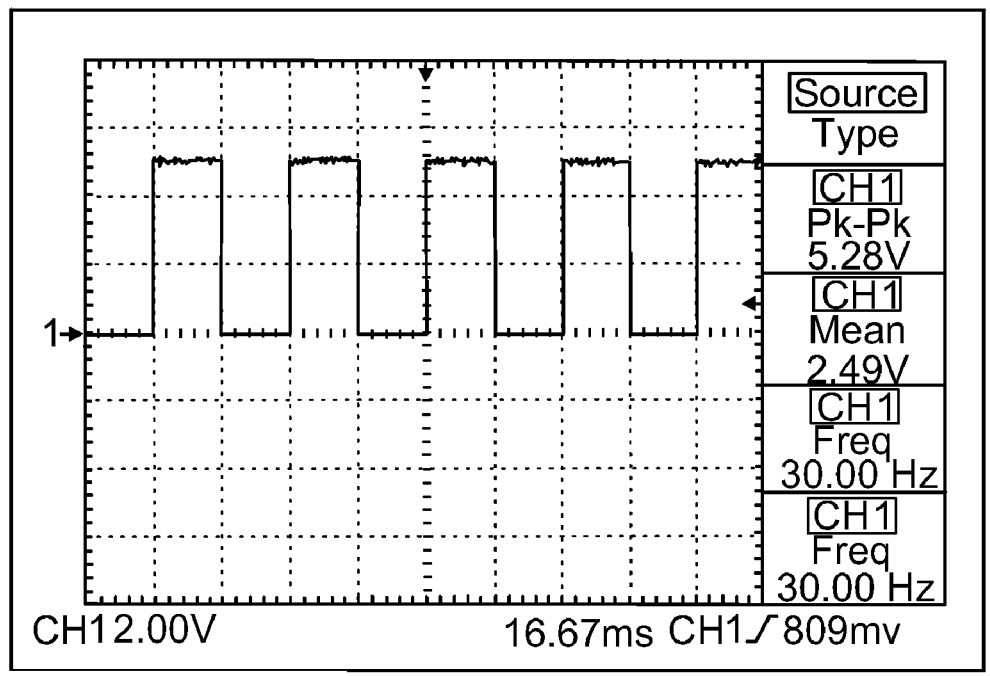
FIG. 3 illustrates an example voltage waveform output by the apparatus of FIG. 2.

As shown in FIG. 2, the example apparatus 200 is electrically interconnected with the system 100 by wires 210 and 220. A first end of the first wire 210 electrically connects to electrode 110 and a first input of the EEG amplifier 140, whereas a first end of the second wire 220 electrically connects to electrode 120 and a second input of the EEG amplifier 140. Second ends of the first and second wires 210, 220 connect to an end of a first switch d0 230 (e.g., a double-pole, single-throw switch, two single-pole, single-throw switches, or any other switching devices suitable for this application including, for example field effect transistors (FETs), bipolar junction transistors (BJTs), etc.), the other end of which is connected with a resistor-switch arrangement 240. As shown, the resistor-switch arrangement 240 includes three switches d1, d2, d3 and two resistors R1 and R2. A controller such as a microprocessor or microcontroller 250 is connected with the resistor-switch arrangement 240 and switch d0 230 for controlling the switches. Additionally, the microprocessor or microcontroller 250 may determine electrode impedances relative to measured voltages and known resistances, both of which result from selective opening and closing of the switches. The microcontroller 250, which as shown is supplied by a 5 VDC power source, pulses a digital output line 260 to generate a voltage signal that is suitable for the selected application. Although the microcontroller 250 is shown in FIG. 2 to be outputting the voltage signal, it should be appreciated that the microcontroller 250 may alternatively control a voltage source such as a signal or function generator for outputting the voltage signal. As shown in FIG. 2, the voltage signal output by the microcontroller 250 may have a frequency/repetition rate of about 30 Hz. As shown in FIG. 3, one example voltage signal may be a square wave with a 30 Hz repetition rate, 50% duty cycle and switching between 0 VDC and 5 VDC. However, it can be appreciated that the voltage signal can have other properties. Indeed, this base frequency, duty cycle and amplitude could be modified as necessary for any particular application. 30 Hz was chosen for EEG applications in this example, as this frequency is far from the frequency of larger amplitude EEG signals that are also present during measurement. However, other frequencies such as, for example, 20 Hz and frequencies in the range of about 20 Hz to about 30 Hz also work well for EEG applications.

Figure 4:
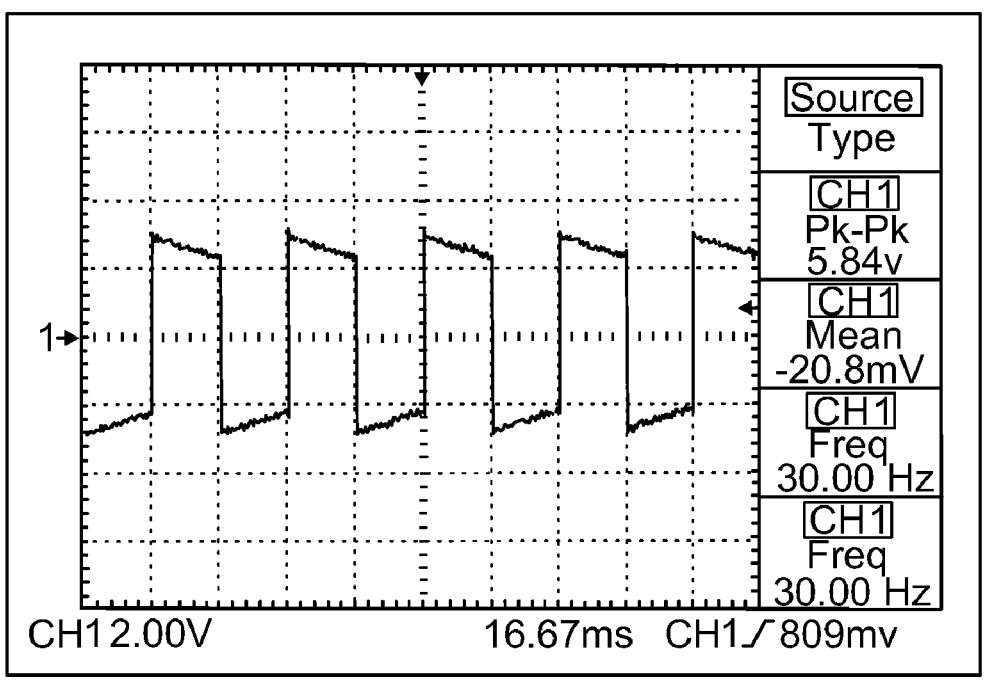
FIG. 4 illustrates the example voltage waveform of FIG. 3 after conversion to bipolar form.

A capacitor 270 was configured in series with an output of the digital output line 260 to convert the unipolar output to a bipolar output as seen in FIG. 4. A bipolar output signal may be preferred in some instances to prevent electrode polarization, which can have a negative influence on resulting signal quality. Bipolar signals tend to depolarize electrodes, which is beneficial.

A voltage divider 280 is configured in series between the capacitor 270 and the resistor-switch arrangement 240 to reduce the output signal level. The particular signal level that is shown, $V_{in}$=280 μVpk, was chosen to match the dynamic range of the selected EEG amplifier 140 while still preserving adequate measurement resolution. However, other signal levels may be suitable as well and should be selected as appropriate for the intended application and hardware being used. For example, larger $V_{in}$ values can improve measurement resolution, but can also saturate the EEG amplifier 140 if proper care is not taken.

In addition to outputting the voltage signal or controlling a voltage source to output the voltage signal, the microcontroller 250 controls first switch d0 230 and switches d1-d3 of resistor-switch arrangement 240. The switches d0-d3 may be inexpensive and commonly available, such as field effect transistors (FETs). However, switches d0-d3 may be other electrically controllable switching devices known in the art such as solenoid-actuated microswitches, bipolar junction transistors (BJTs), etc.

When determining impedances, the microcontroller 250 operates the switches d0-d3 to energize various electrical signal paths in order to obtain multiple independent voltage measurements. Each measurement ($V_{amp}$) is digitized and stored. When each of the three combinations of switches has been set and the data acquired for a predetermined period of time (e.g., approximately 0.2 seconds for each path), the combined measurements are processed using either a frequency domain or time domain algorithm (run by a processor such as microcontroller 250, DSP 170 or other external computing device (e.g., a PC)) that computes the impedances of the three electrodes from the voltage signal data that has been collected.

The presently described embodiment of the apparatus has four basic operating modes, each mode described by a distinct configuration of switch positions. The modes are provided in Table 1.

TABLE 1

| Mode | Description | d0 | d1 | d2 | d3 |
|---|---|---|---|---|---|
| 1 | Measurement 1 | Closed | Open | Closed | Open |
| 2 | Measurement 2 | Closed | Closed | Open | Open |
| 3 | Measurement 3 | Closed | Open | Open | Closed |
| 4 | No Measurement | Open | Closed | Closed | Open |

When the system is in Mode 4 (No Measurement), the EEG acquisition system 100 functions normally (i.e. the impedance measurement apparatus 200 is electrically isolated from system 100 and is not active). In this mode, it may be desirable to disable or suspend the oscillator output from microcontroller 250. For convenience of explanation, the number of measurement Modes generally corresponds to the number of electrodes in a one-to-one relationship. However, it can be appreciated that the number of Modes may be greater or less than the number of electrodes depending on, for example the configuration of the apparatus 200, particularly the arrangement 240.

To determine the electrode impedances, the microcontroller 250 controls the apparatus 200 to cycle through Modes 1-3. Although the present apparatus and method is described hereafter as sequentially cycling through Modes 1-3, it should be understood that this is not limiting the invention. Indeed, the Modes may be activated in different orders or even in a random order. Furthermore, it should be appreciated that the number of Modes is not limiting the invention. Additional modes could be added, but, as a minimum, it is desirable to obtain at least one measurement for each electrode being tested for three or more electrodes. Furthermore, fewer Modes may be used as will be described hereafter.

Starting with Mode 1, the $V_{amp}$ signal (i.e., output from amplifier 140) is acquired and stored for approximately 0.2 seconds. Similarly, data is acquired and stored during Modes 2 and 3. Diagrams illustrating equivalent circuit diagrams related to the various Modes and the switch conditions follow hereafter.

Obtaining the Measurements

Figure 5:
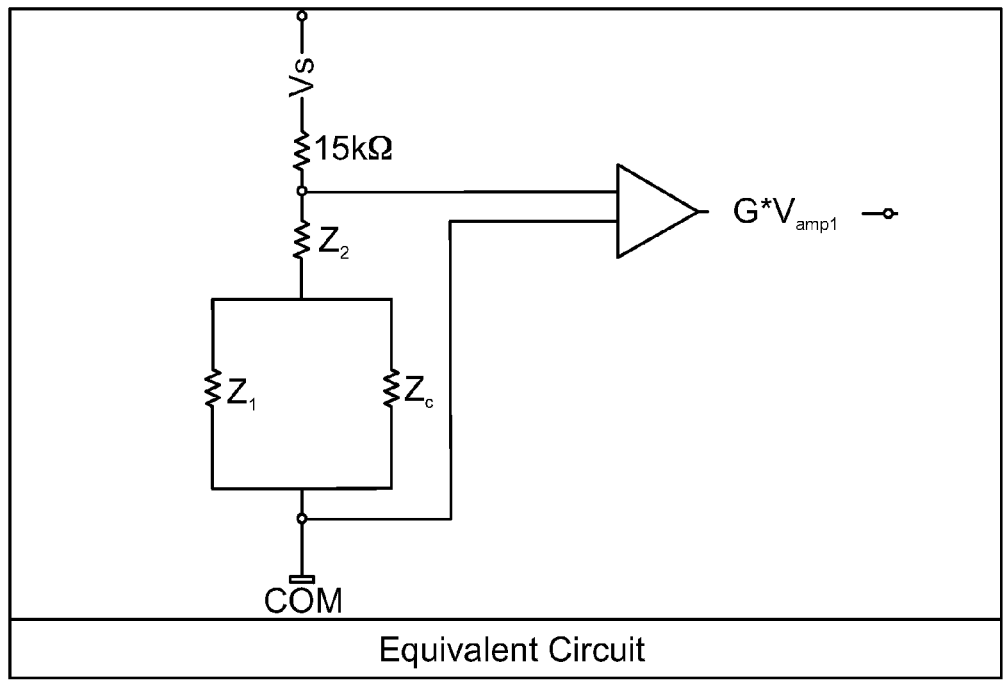
FIGS. 5-8 illustrate equivalent circuit diagrams of the apparatus of FIG. 2 which occur during various operating modes of the apparatus.

In Mode 1, switches d0 and d2 are closed whereas switches d1 and d3 are opened. By closing d2 one input of the amplifier (i.e., the input connected with electrode 110) becomes connected to ground (com). The equivalent circuit shown in FIG. 5 illustrates the resulting configuration of the resistor-switch arrangement 240. In FIG. 5, $V_s$ is 280 μVpk at 30 Hz and $G*V_{amp1}$ denotes the output voltage measurement from the amplifier 140 obtained during Mode 1 with G being the amplifier gain. In one example embodiment G=2250 at 30 Hz. From Mode 1 the following equation is obtained:

$$Z_2 + \frac{Z_c Z_1}{Z_c + Z_1} = m_1 \quad \text{(equation 1)}$$

Letting $V_{amp1}$ denote the voltage input to amplifier 140 during Mode 1, it follows that:

$$m_1 = \frac{V_{amp1}}{\left(\frac{V_s - V_{amp1}}{15 \text{ k}\Omega}\right)}$$

Figure 6:
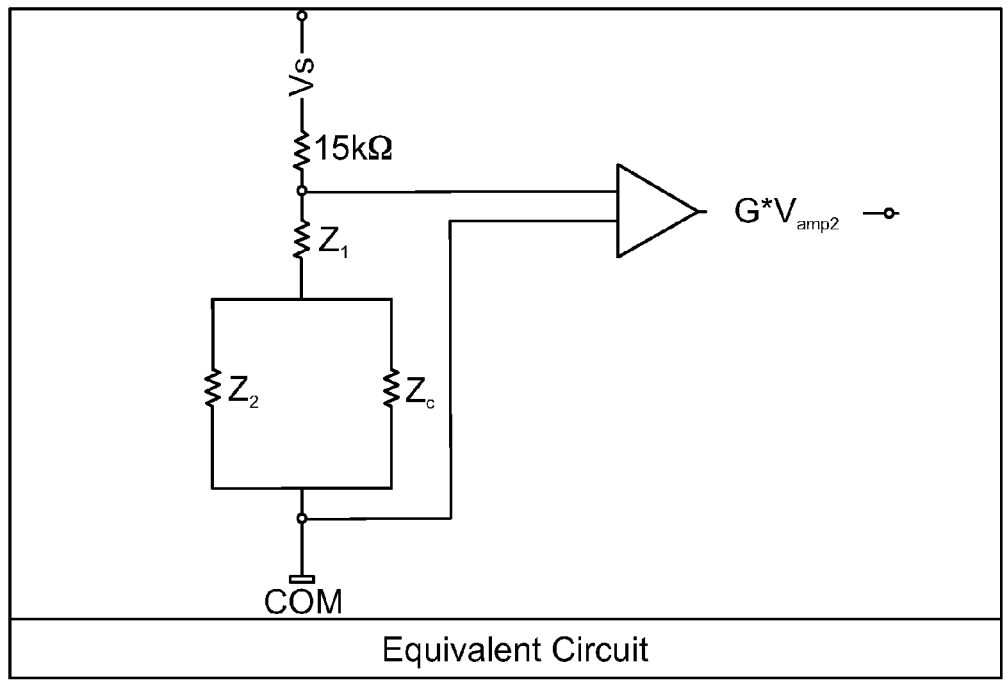

In Mode 2, switches d0 and d1 are closed whereas switches d2 and d3 are opened. By closing d1 a different input of the amplifier (i.e., the input connected with electrode 120) becomes connected to ground (com). The equivalent circuit shown in FIG. 6 illustrates the resulting configuration of the resistor-switch arrangement 240. From Mode 2 the following equation is obtained:

$$Z_1 + \frac{Z_c Z_2}{Z_c + Z_2} = m_2 \quad \text{(equation 2)}$$

Letting $V_{amp2}$ denote the voltage input to amplifier 140 during Mode 2, it follows that:

$$m_2 = \frac{V_{amp2}}{\left(\frac{V_s - V_{amp2}}{15 \text{ k}\Omega}\right)}$$

In Mode 3, switches d0 and d3 are closed whereas switches d1 and d2 are opened. By closing d3, resistor R2 is bypassed.

Figure 7:
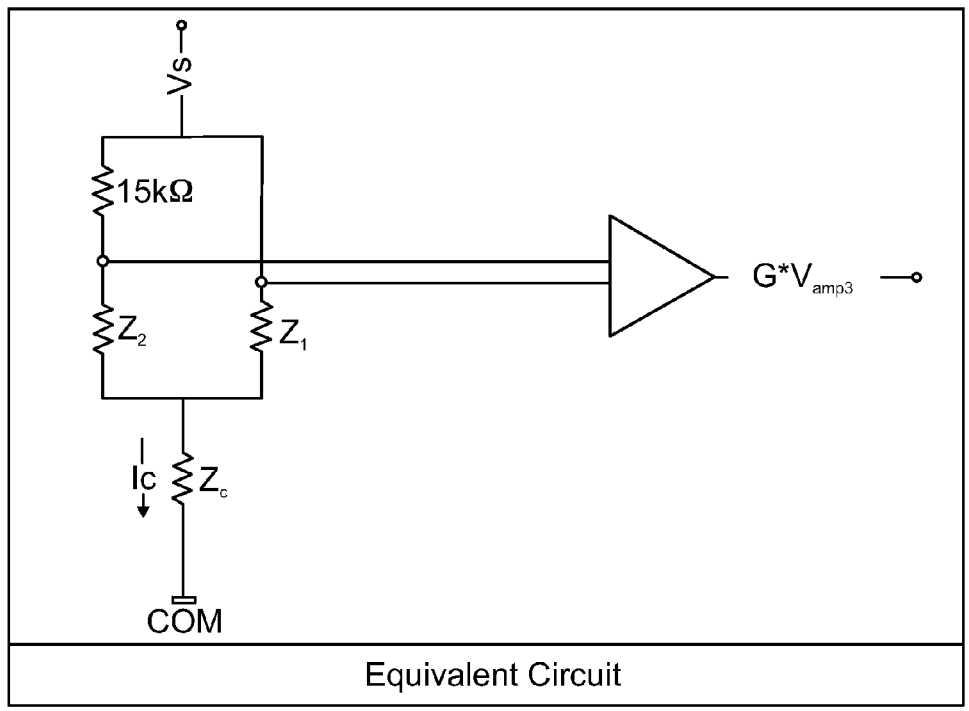

The equivalent circuit shown in FIG. 7 illustrates the resulting configuration of the resistor-switch arrangement 240. From Mode 3 the following equation is obtained:

$$\frac{V_s}{\left(Z_c + \frac{Z_1(Z_2 + 15\ k\Omega)}{Z_1 + Z_2 + 15\ k\Omega}\right)} = I_c \quad \text{(equation 3)}$$

Letting $V_{amp3}$ denote the voltage input to amplifier 140 during Mode 3, it follows that:

$$I_c = \frac{V_s - \frac{15\ K\Omega + Z_2}{15\ K\Omega} V_{amp3}}{Z_c}$$

Figure 8:
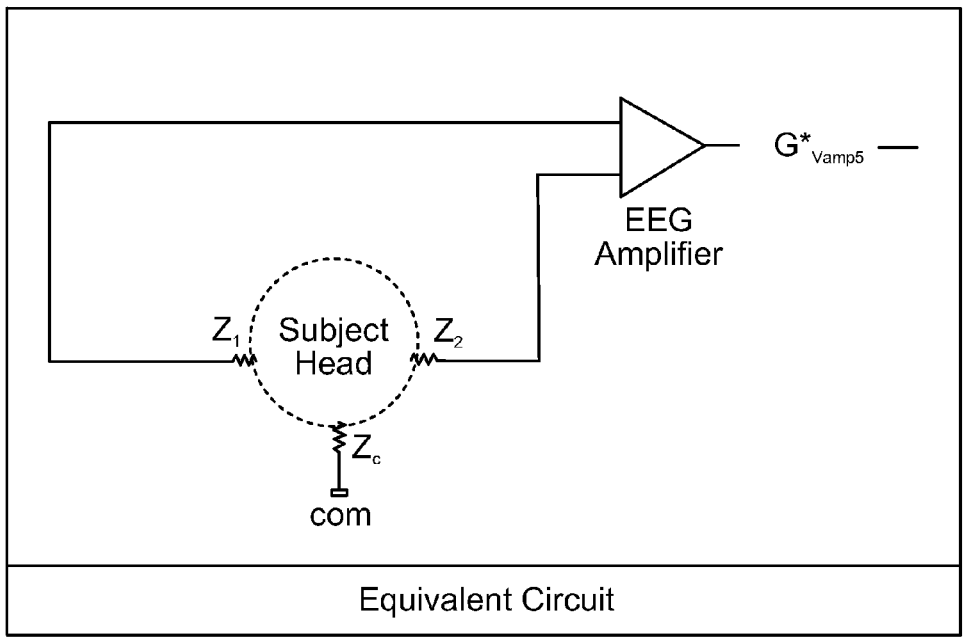

In Mode 4, switch d0 is open. Accordingly, the equivalent circuit shown in FIG. 8 illustrates the resulting (no measurement) configuration of the resistor-switch arrangement 240. The source signal may be disabled by the microcontroller 250 i.e., source signal $V_s$ may be 0 VDC. $G*V_{amp5}$ denotes the output voltage measurement from the amplifier 140 during this condition. While the apparatus 200 is operating in Mode 4, the system 100 may operate normally for measuring/recording a subject's EEG or other physiologic signals.

Computing the Electrode Impedances

The computed values of $Z_1$, $Z_2$ and $Z_c$ (i.e., the electrode impedances to be determined) are obtained by solving the foregoing algebraic equations associated with Modes 1, 2 and 3. As can be appreciated from the foregoing equations, the electrode impedances are expressed in terms of known impedance values and measured voltages. Accordingly, the simultaneous equations for $Z_1$, $Z_2$ and $Z_c$ can been solved explicitly in terms of the measured $V_{amp1}$, $V_{amp2}$, and $V_{amp3}$ voltage values. Solutions for the electrode impedances are given hereafter.

Figure 9:
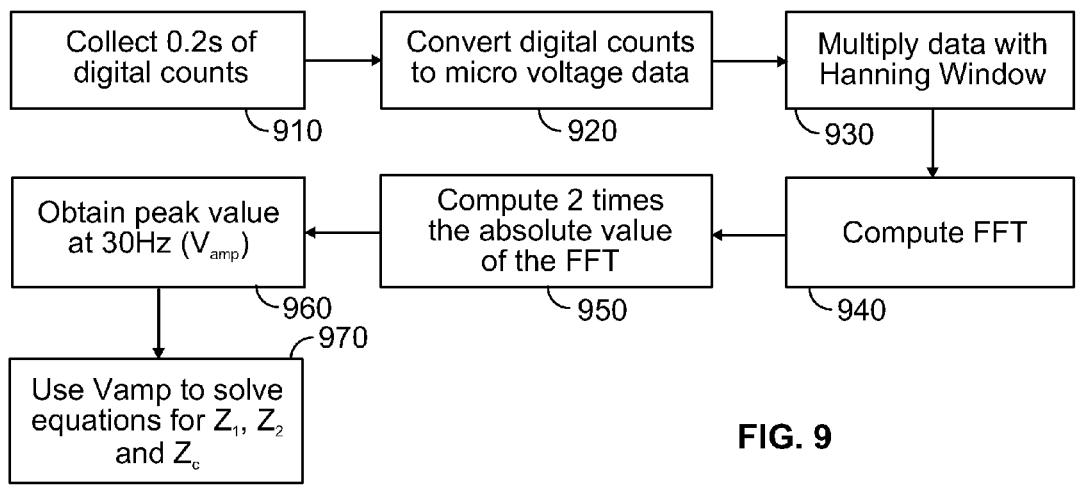
FIG. 9 illustrates a flowchart showing an example method for determining electrode impedances according to another aspect of the present invention.
Figure 10A:
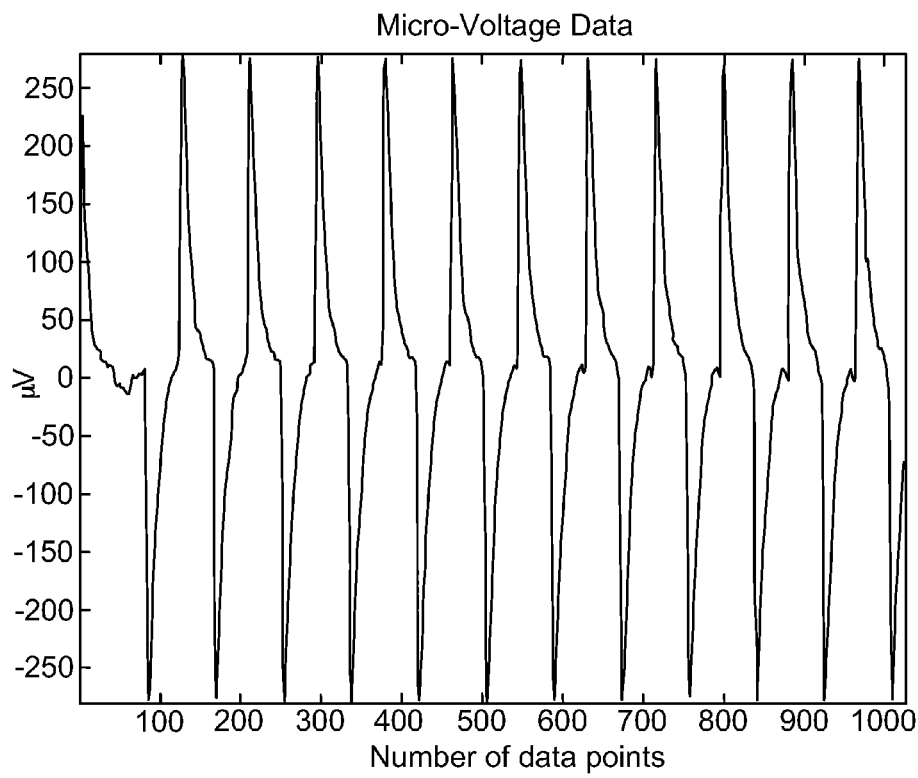
FIG. 10A illustrates an example waveform of micro-level voltage data obtained during the method of FIG. 9.
Figure 10B:
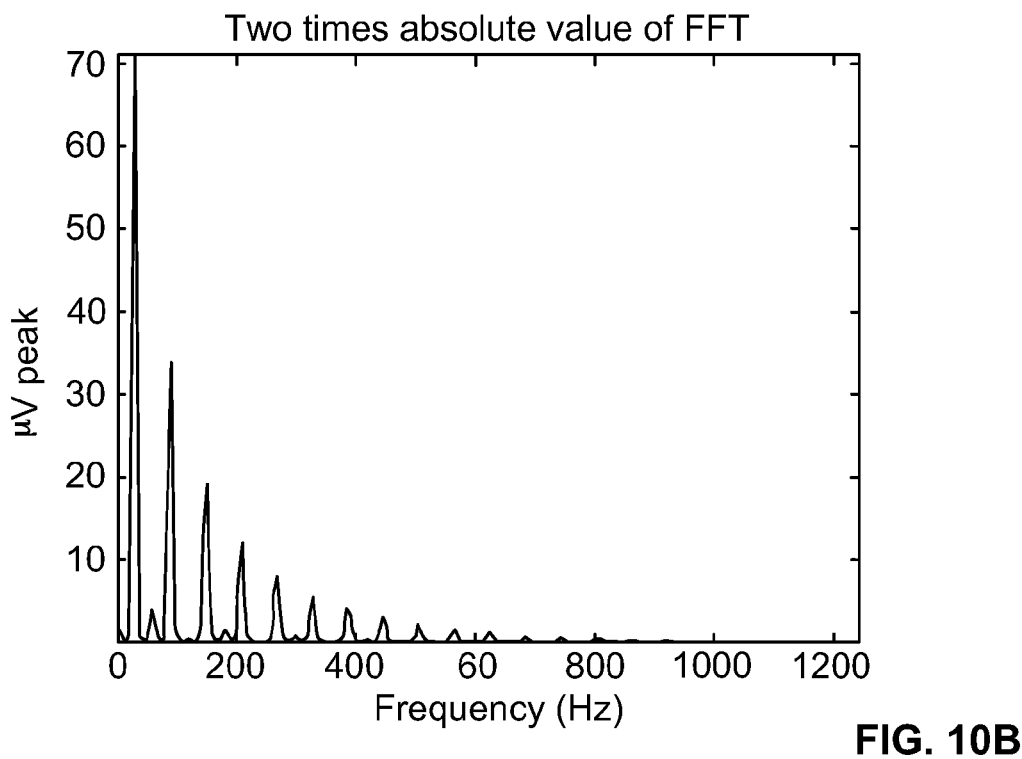
FIG. 10B illustrates the example waveform of FIG. 10A after conversion to the frequency domain according to the method of FIG. 9.
Figure 11:
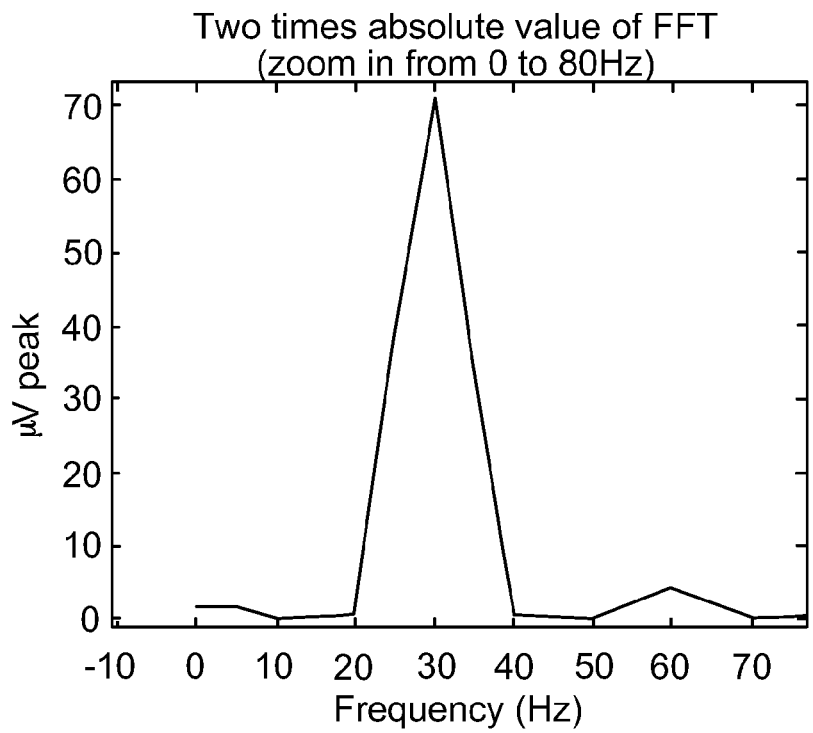
FIG. 11 illustrates a close-up view of a portion of the waveform of FIG. 10B showing identification of the peak value during the method of FIG. 9.

An example method for determining the electrode impedances is shown in FIG. 9. In step 910 of the example method 0.20 seconds of digital counts are collected for each of the voltages $V_{amp1}$, $V_{amp2}$, and $V_{amp3}$. Next, in step 920, the digital counts are converted to micro-level voltage data. An example plot of micro-level voltage data is shown in FIG. 10A. In order to minimize the influence of extraneous noise (e.g., physiologic signals, 60 Hz line interference, etc.), the final $V_{amp}$ voltage value waveforms are converted to the frequency domain. As shown in step 930, the final $V_{amp}$ voltage values are computed using a window function (e.g., a Hanning window) on 0.20 seconds of $V_{amp}$ data. Next, in step 940 the Fast Fourier Transformation (FFT) is used to transform the time domain data into the frequency domain (this, and other suitable methods, are well known to those skilled in signal processing). In step 950, two times the absolute value of the FFT (except for DC) is computed to generate the peak Voltage Spectrum. An example plot of the micro-level voltage data of FIG. 10A after step 950 is shown in FIG. 10B. In step 960, the peak voltage for the 30 Hz measurement can be obtained from the maximum power value at 30 Hz. Alternatively, if more or less than 0.20 seconds of data is used, the frequency resolution of the resulting voltage spectrum would not have 30 Hz as an explicit frequency value. Therefore, the peak voltage for the 30 Hz measurement could be obtained by selecting the maximum voltage between two adjacent frequencies on the Voltage Spectrum that include 30 Hz in the frequency range (e.g. 20 to 40 Hz). An example plot of the 30 Hz peak is shown in FIG. 11.

Although the windowed Voltage Spectrum was used in the above embodiment, one could also choose to compute the Power Spectral Density (PSD) instead of the Voltage Spectrum, or use an equivalent time-domain implementation, or any such computation that is known to those versed in the art.

After obtaining the peak voltage values in step 960, these voltage values are used to solve the equations for the electrode impedances (i.e., $Z_1$, $Z_2$ and $Z_c$). For example, the DSP 170 (FIG. 2), controller 250 (FIG. 2) or computer receiving the voltage values may execute a program, algorithm, instructions or the like which use the equations given hereinafter to calculate the electrode impedances.

Sample Waveforms

Referring now to FIGS. 10A, 10B and 11, the foregoing-described method is further described. As shown in FIG. 10A, the waveform plot shows the analog output of the EEG amplifier as digitized (e.g., using a 16-bit A/D converter) and converted to microvolts (native measurement units for EEG signals). One could optionally select an A/D with fewer bits of digitizer resolution. For example, we have observed that voltage measurements for this application acquired with 12 bits of A/D resolution work just as well as those acquired with 16 bits of A/D resolution.

With each change to a new Mode (e.g., switching from Mode 1 to Mode 2, etc.), a transient in the data may occur as the amplifiers settle into the new mode. This transition can last from several milliseconds to several seconds depending upon the particular amplifier characteristics and filter settings. A transient in the data can be observed in the FIG. 10A from points 0 to about 80 (approximately 32 ms). Therefore, it may be beneficial in the method (e.g., in step 920) to skip a predetermined number of data points such that the amplifiers have time to settle. For example, the first 150 data points may be skipped in order to ensure that the data is not affected by the mode switching or other transition points in the data when a measurement is taken.

The time domain data is then multiplied by a window function and the Voltage Spectrum is computed. FIG. 10B shows the time domain data of FIG. 10A after multiplying the data by a Hanning window function and transformation into the frequency domain using the FFT. In FIG. 10B, the peak voltage value at each frequency from DC through 1250 Hz is shown. Because the oscillator source signal is about 30 Hz, we are interested in voltage values near 30 Hz. FIG. 11 shows a close-up view of the waveform plot of FIG. 10B focusing on the range of 0 to about 80 Hz. The peak amplifier voltage value at or around 30 Hz during Mode M, with M=1, 2 and 3 as discussed previously, is used as $V_{ampM}$.

After obtaining $V_{amp1}$, $V_{amp2}$ and $V_{amp3}$ in the manner described above, these values are used in the following equations to compute the values of $Z_1$, $Z_2$ and $Z_c$.

Explicit solutions for $Z_1$, $Z_2$ and $Z_c$ are as follows:

$$Z_1 = m_2 \cdot V_{amp3} \cdot m_1 \cdot V_s \cdot R \cdot (R + m_1)/(-m_2 \cdot V_{amp3}^2 \cdot m_1^2 + (V_s^2 \cdot R^2 + 2V_{amp3} \cdot m_2 \cdot V_s \cdot R - 2R \cdot m_2 \cdot V_{amp3}^2) \cdot m_1 + 2R^2 \cdot V_s \cdot m_2 \cdot V_{amp3} - R^2 \cdot m_2 \cdot V_{amp3}^2 - R^2 \cdot V_s^2 \cdot m_2) \quad \text{(equation 4)}$$

$$Z_2 = R \cdot V_s \cdot m_1 \cdot ((m_2 \cdot V_{amp3} + V_s \cdot R) \cdot m_1 + R \cdot m_2 \cdot V_{amp3} - m_2 \cdot V_s \cdot R)/(-m_2 \cdot V_{amp3}^2 \cdot m_1^2 + (V_s^2 \cdot R^2 + 2V_{amp3} \cdot m_2 \cdot V_s \cdot R - 2R \cdot m_2 \cdot V_{amp3}^2) \cdot m_1 + 2R^2 \cdot V_s \cdot m_2 \cdot V_{amp3} - R^2 \cdot m_2 \cdot V_{amp3}^2 - R^2 \cdot V_s^2 \cdot m_2) \quad \text{(equation 5)}$$

$$Z_c = ((m_1 - Z_2) \cdot Z_2)/(Z_1 + Z_2 - m_1) \quad \text{(equation 6)}$$

where:
R = 15 kΩ;
m1 = $V_{amp1}/((V_s - V_{amp1})/R)$; and
m2 = $V_{amp2}/((V_s - V_{amp2})/R)$.

FIGS. 12A-23A illustrate equivalent circuit diagrams according to the apparatus 200 of FIG. 2 operating in the various Modes (i.e., Modes 1, 2 and 3) for explaining various electrode fault conditions (e.g., when an electrode is fully disconnected from the patient). FIGS. 12B-23B illustrate amplifier output waveforms in the time domain for the three Modes and the various electrode fault conditions corresponding to FIGS. 12A-23A, respectively. FIGS. 12C-23C illustrate amplifier output waveforms in the frequency domain corresponding to FIGS. 12B-23B, respectively.

Figure 12A:
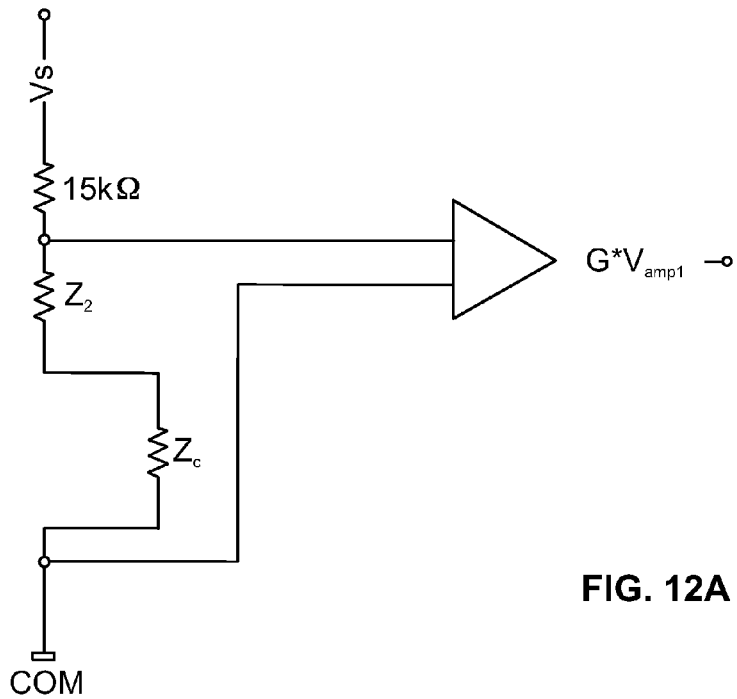
FIGS. 12A-23C illustrate equivalent circuit diagrams of the apparatus of FIG. 2, and corresponding waveforms for explaining various electrode fault conditions.
Figure 12B:
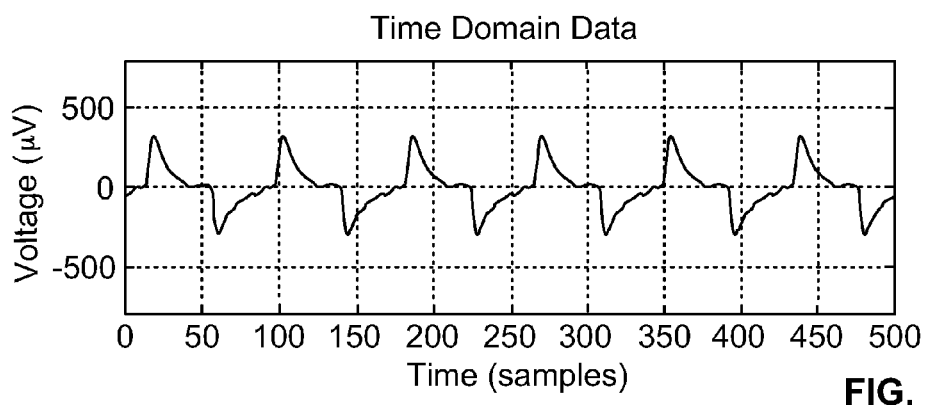
Figure 12C:
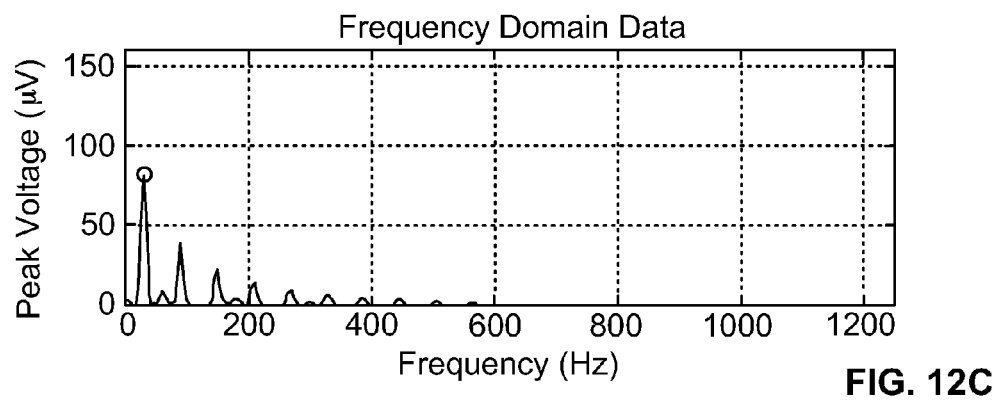
Figure 13A:
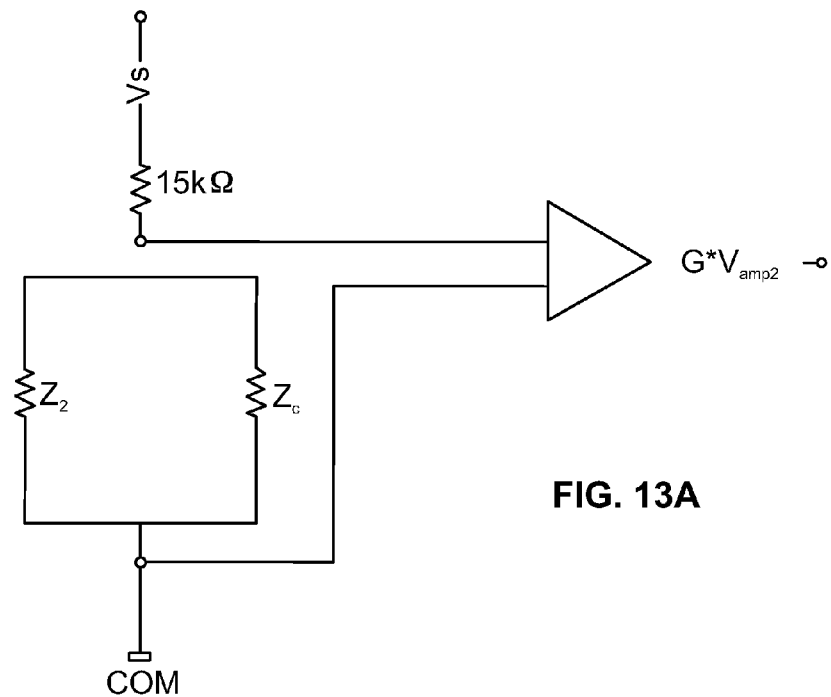
Figure 13B:
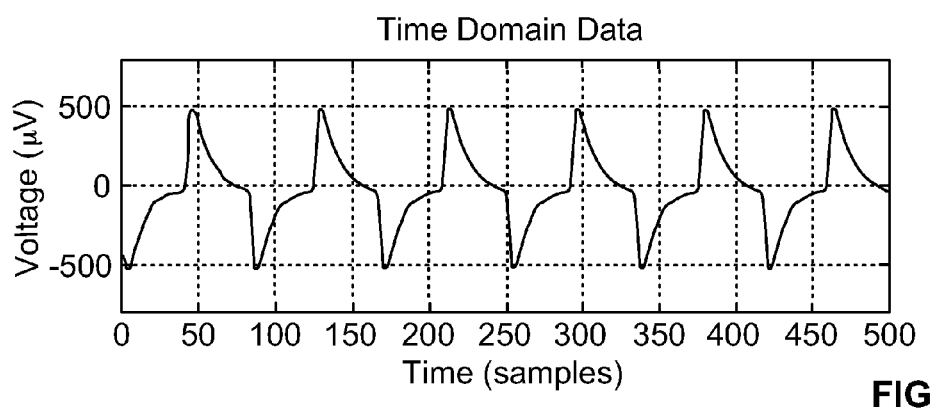
Figure 13C:
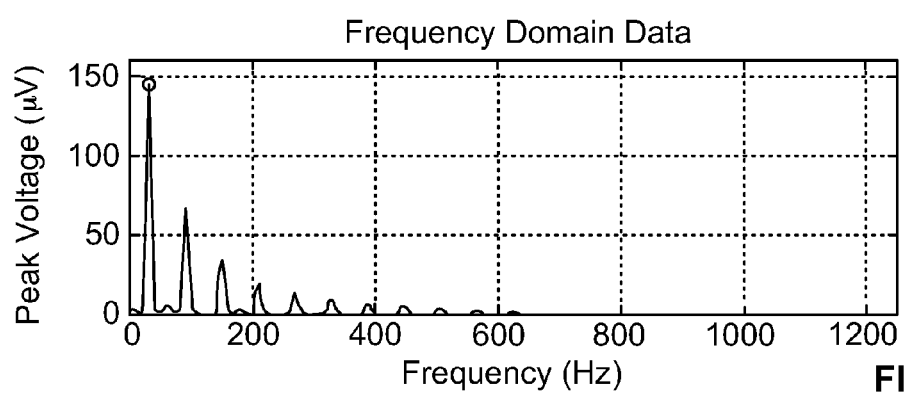
Figure 14A:
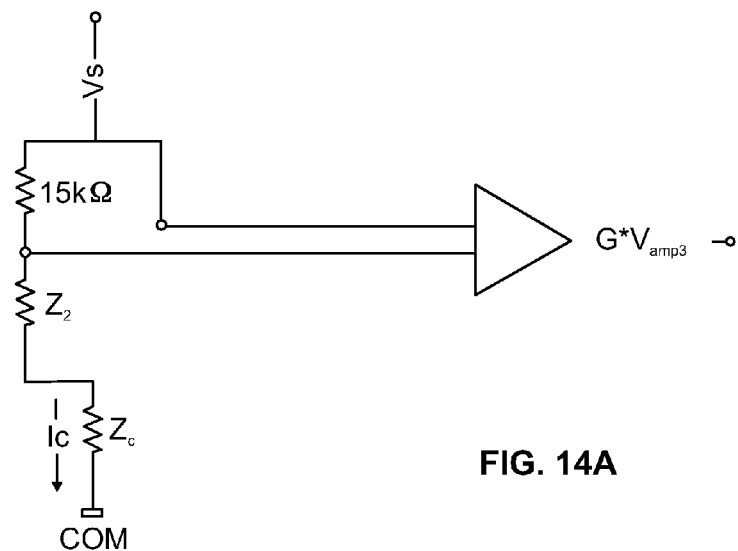
Figure 14B:
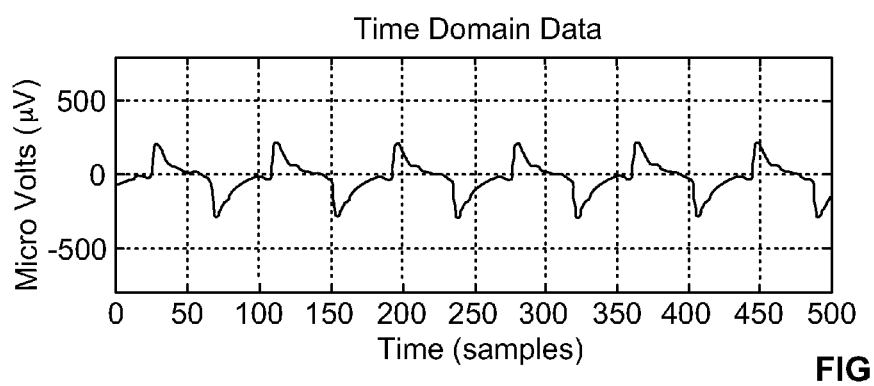
Figure 14C:
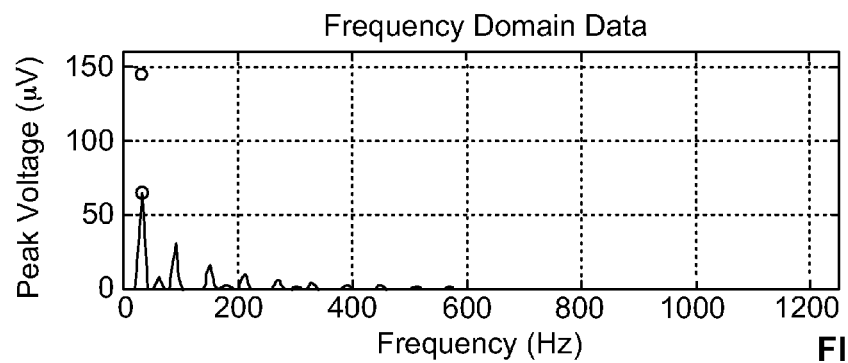

FIGS. 12A-12C, 13A-13C and 14A-14C are provided to show the system 100 (FIGS. 1 and 2) operating in a state with the $Z_1$ electrode being disconnected from the subject (i.e., $Z_1=\infty\Omega$). FIG. 12A shows the apparatus 200 (FIG. 2) operating in Mode 1 and FIGS. 12B and 12C show that $V_{amp1}$ looks like a normal value. FIG. 13A shows the apparatus 200 operating in Mode 2 and FIGS. 13B and 13C show that $V_{amp2}$ is substantially similar to $V_s$ (i.e., $V_{amp2}$ theoretically should be $V_s$). FIG. 14A shows the apparatus 200 operating in Mode 3 and FIGS. 14B and 14C show that $V_{amp3}$ looks like a normal value.

Figure 15A:
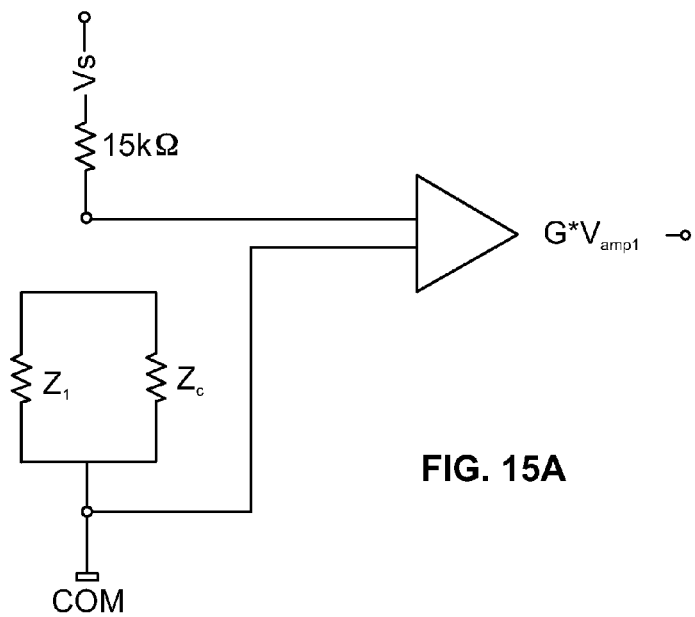
Figure 15B:
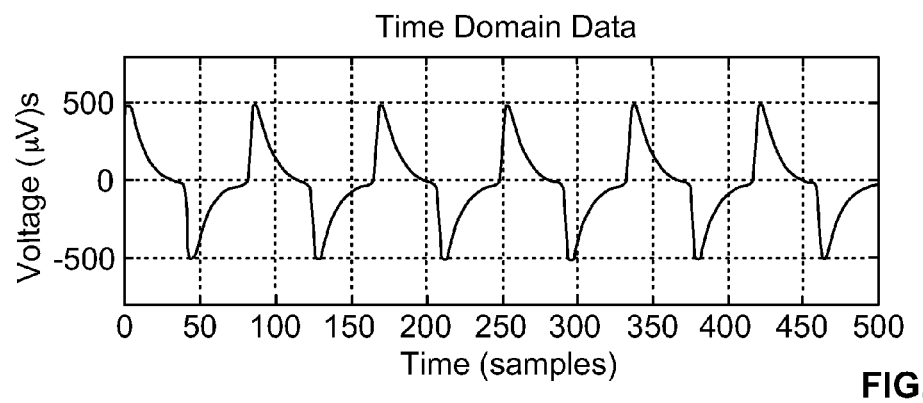
Figure 15C:
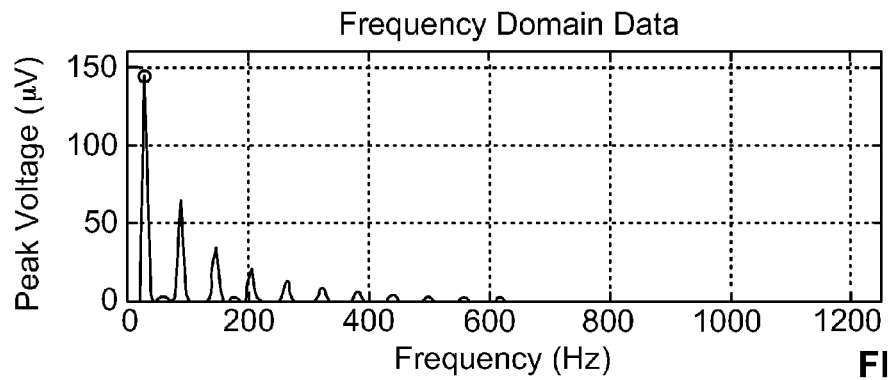
Figure 16A:
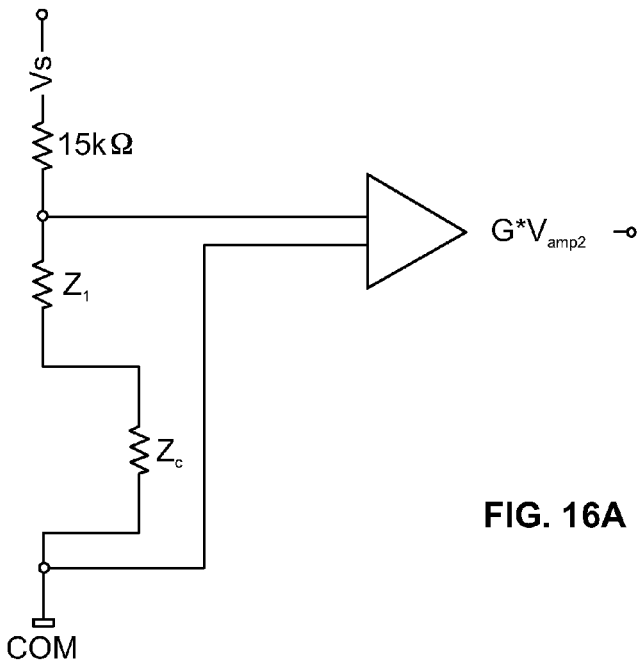
Figure 16B:
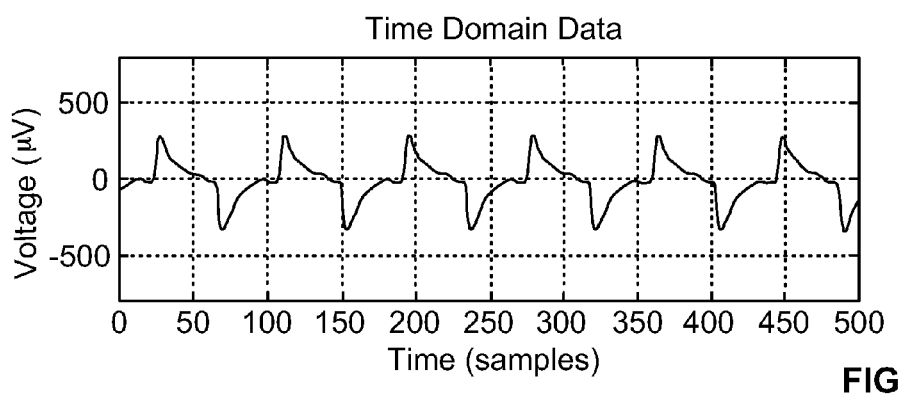
Figure 16C:
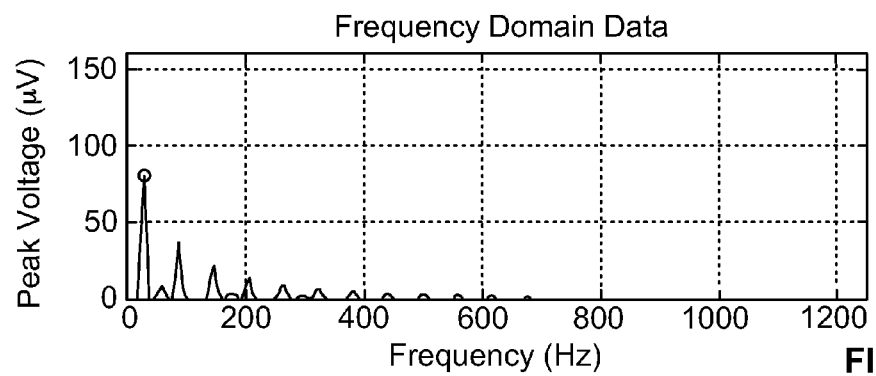
Figure 17A:
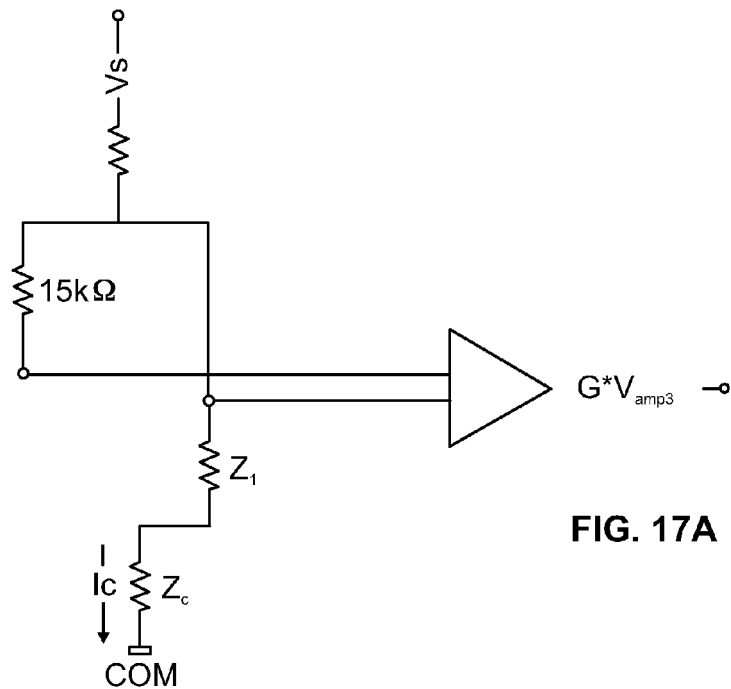
Figure 17B:
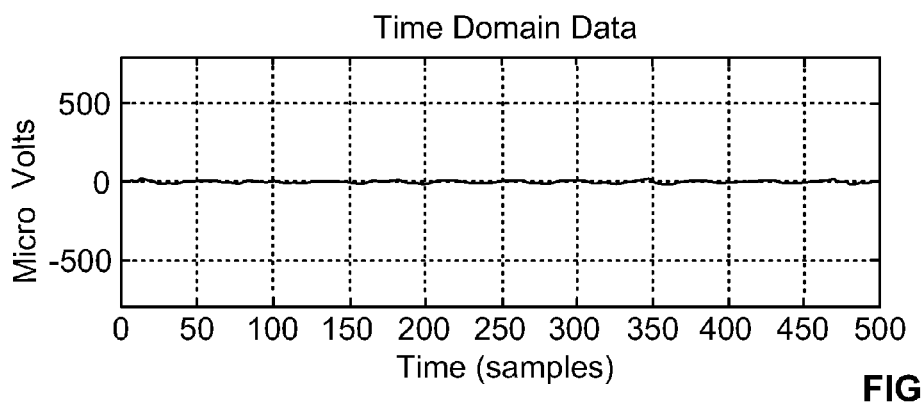
Figure 17C:
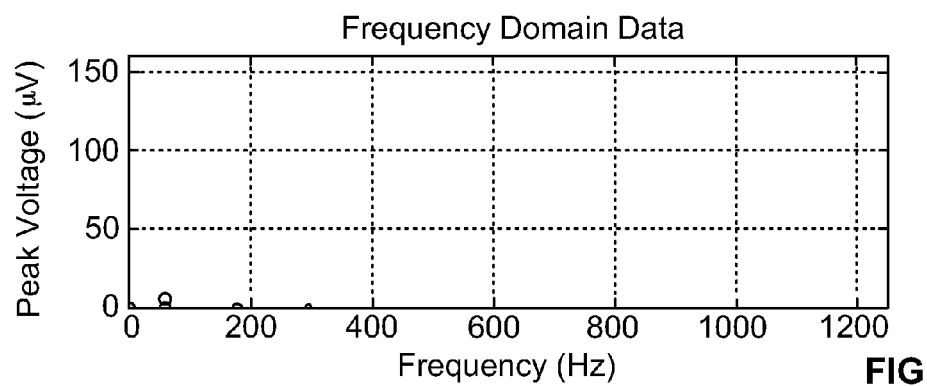

Referring to FIGS. 15A-15C, 16A-16C and 17A-17C, it should be understood that the system 100 (FIGS. 1 and 2) is operating in a state with the $Z_2$ electrode being disconnected from the subject (i.e., $Z_2=\infty\Omega$). FIG. 15A shows the apparatus 200 (FIG. 2) operating in Mode 1 and FIGS. 15B and 15C show that $V_{amp1}$ is substantially similar to $V_s$ (i.e., $V_{amp1}$ theoretically should be $V_s$). FIG. 16A shows the apparatus 200 operating in Mode 2 and FIGS. 16B and 16C show that $V_{amp2}$ looks like a normal value. FIG. 17A shows the apparatus 200 operating in Mode 3 and FIGS. 17B and 17C show that $V_{amp3}$ is very close to zero (i.e., $V_{amp3}$ theoretically should be zero).

Figure 18A:
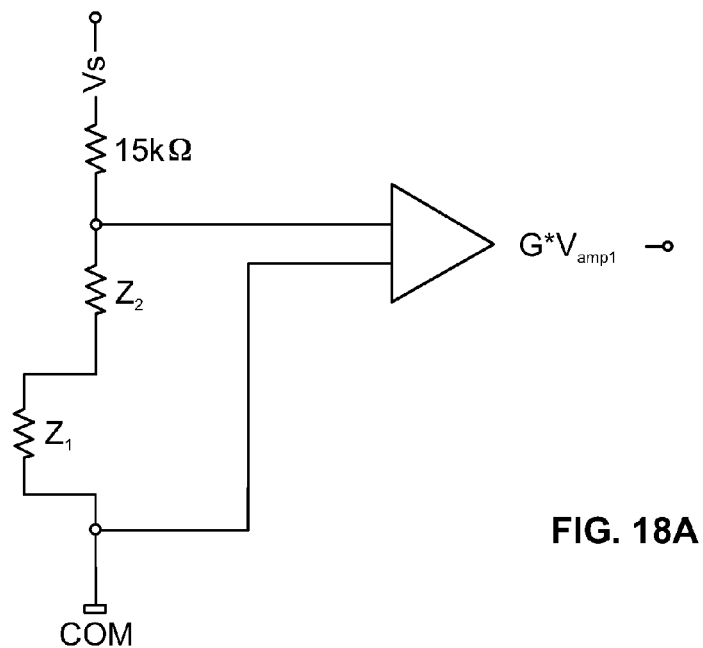
Figure 18B:
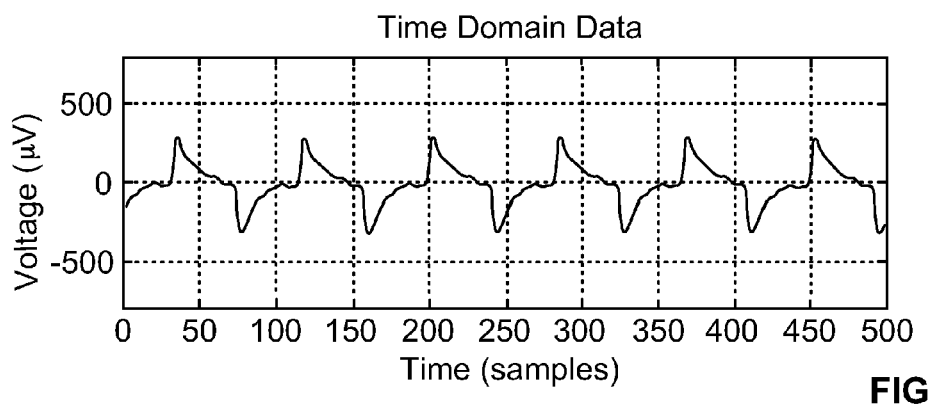
Figure 18C:
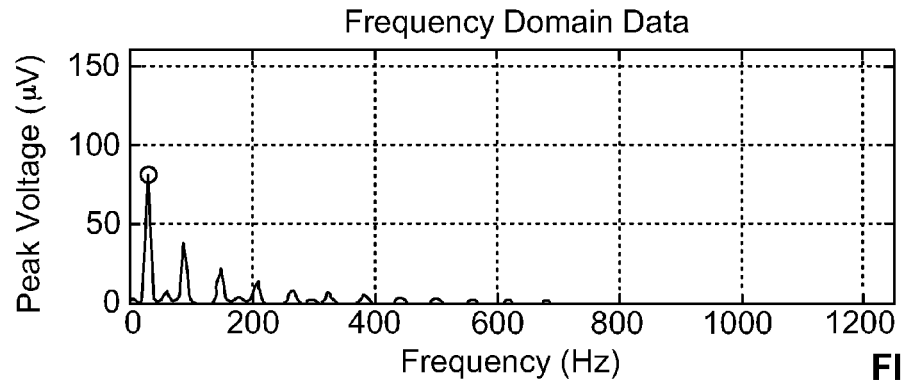
Figure 19A:
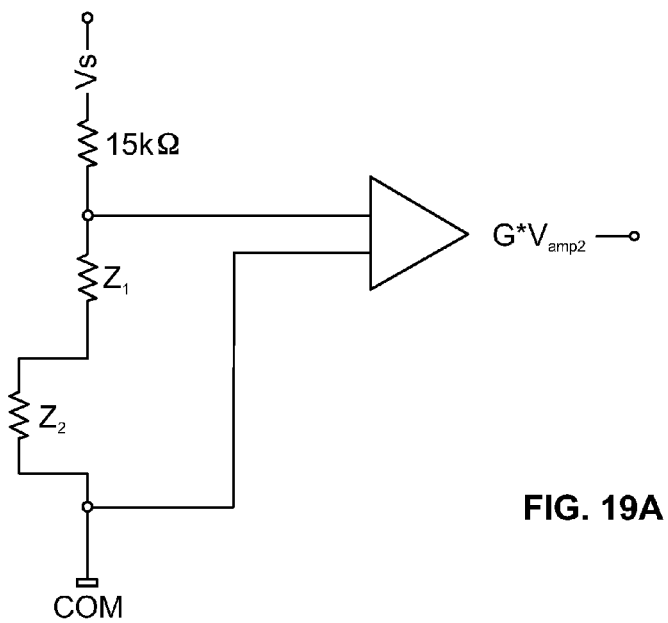
Figure 19B:
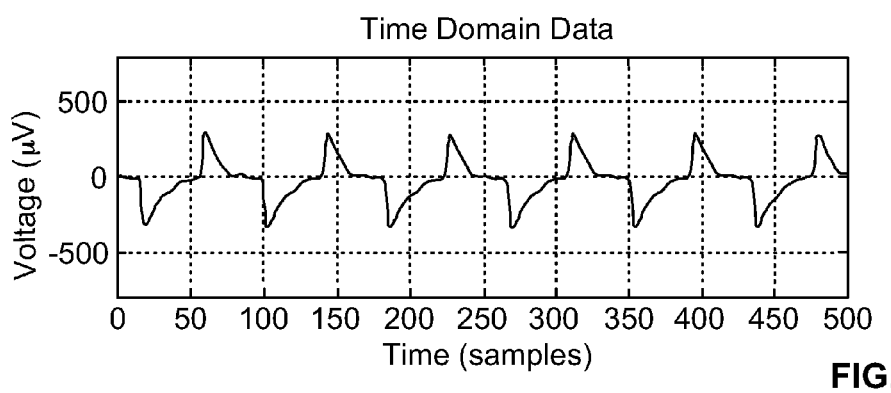
Figure 19C:
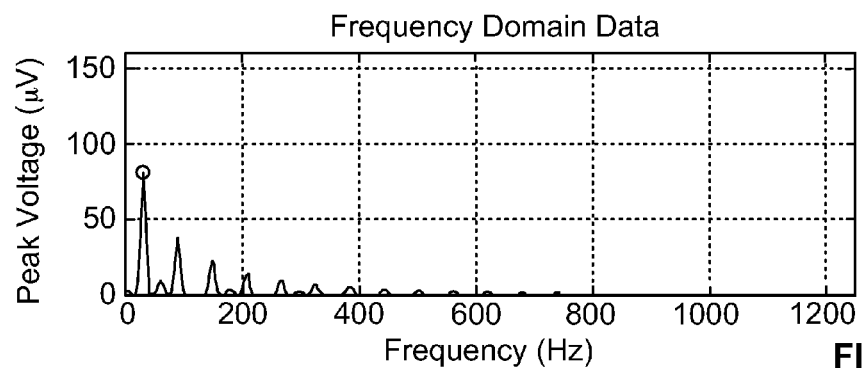
Figure 20A:
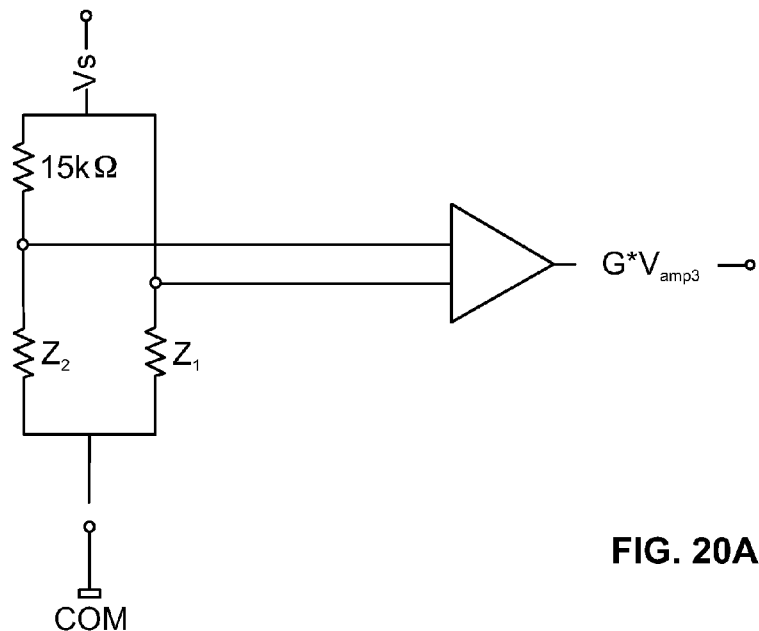
Figure 20B:
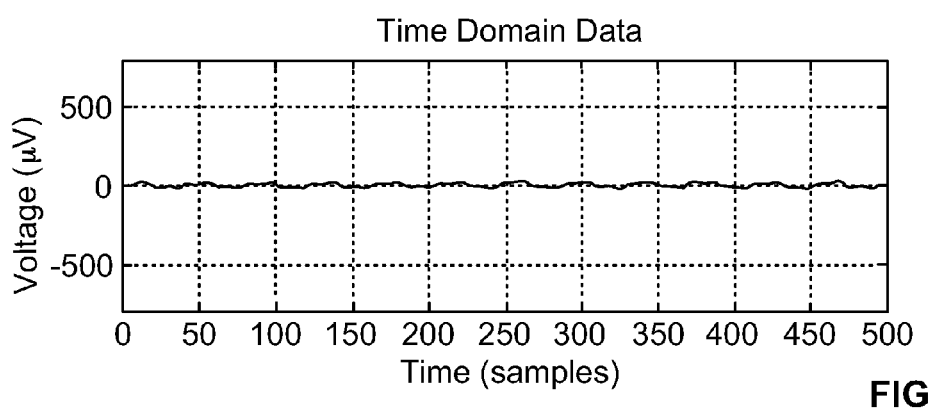
Figure 20C:
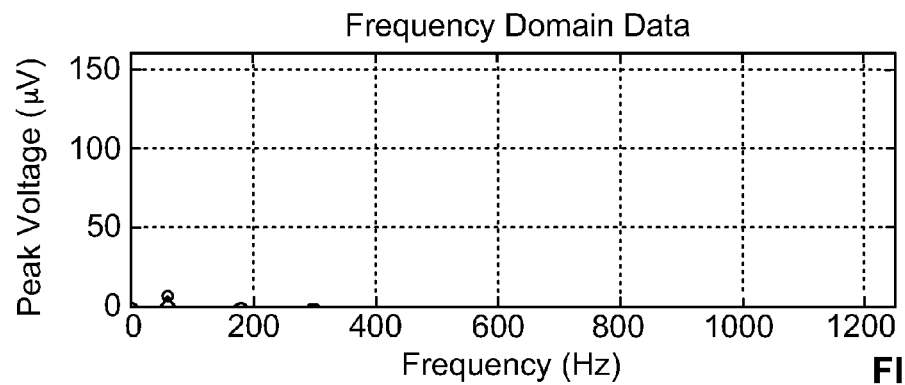

Referring to FIGS. 18A-18C, 19A-19C and 20A-20C, it should be understood that the system 100 (FIGS. 1 and 2) is operating in a state with the $Z_c$ electrode being disconnected from the subject (i.e., $Z_c\infty\Omega$). FIG. 18A shows the apparatus 200 (FIG. 2) operating in Mode 1 and FIGS. 18B and 18C show that $V_{amp1}$ looks like a normal value. FIG. 19A shows the apparatus 200 operating in Mode 2 and FIGS. 19B and 19C show that $V_{amp2}$ looks like a normal value. FIG. 20A shows the apparatus 200 operating in Mode 3 and FIGS. 20B and 20C show that $V_{amp3}$ is very close to zero (i.e., $V_{amp3}$ theoretically should be zero).

Figure 21A:
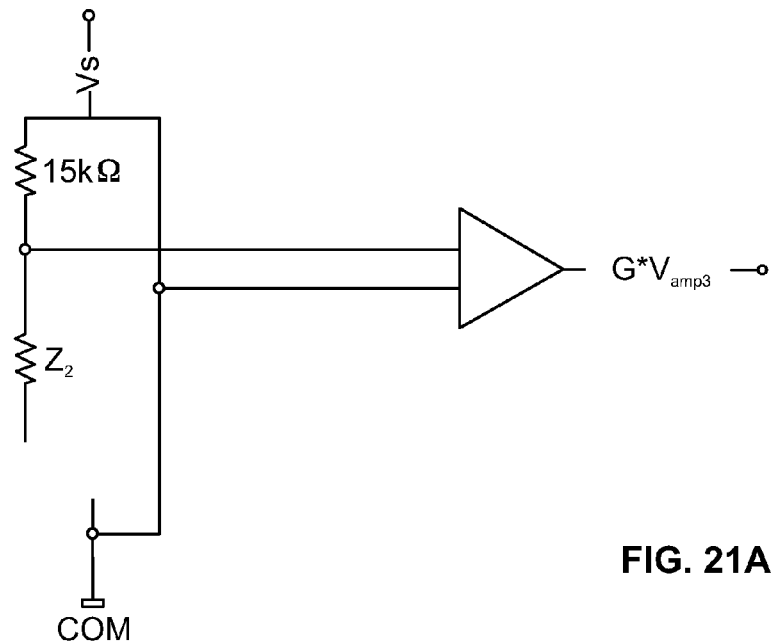
Figure 21B:
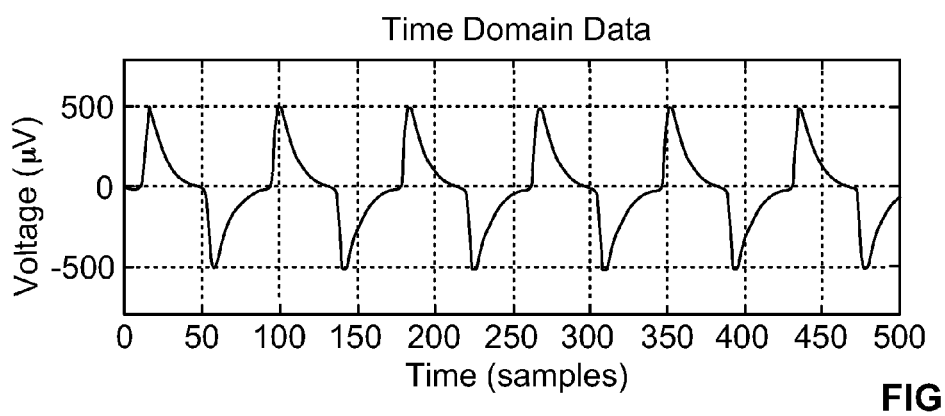
Figure 21C:
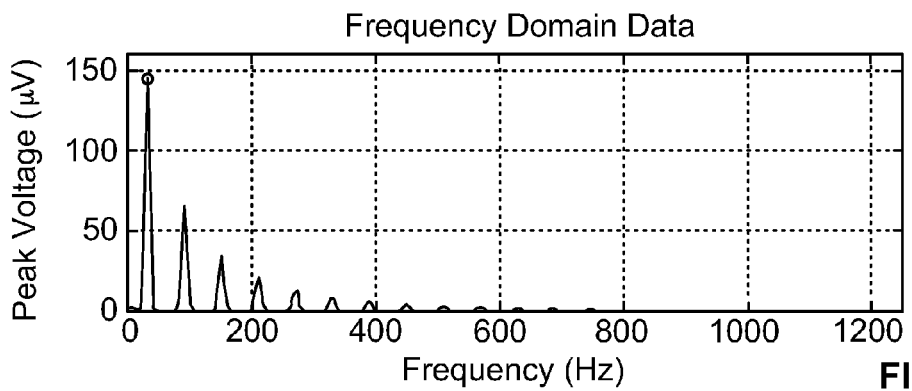
Figure 22A:
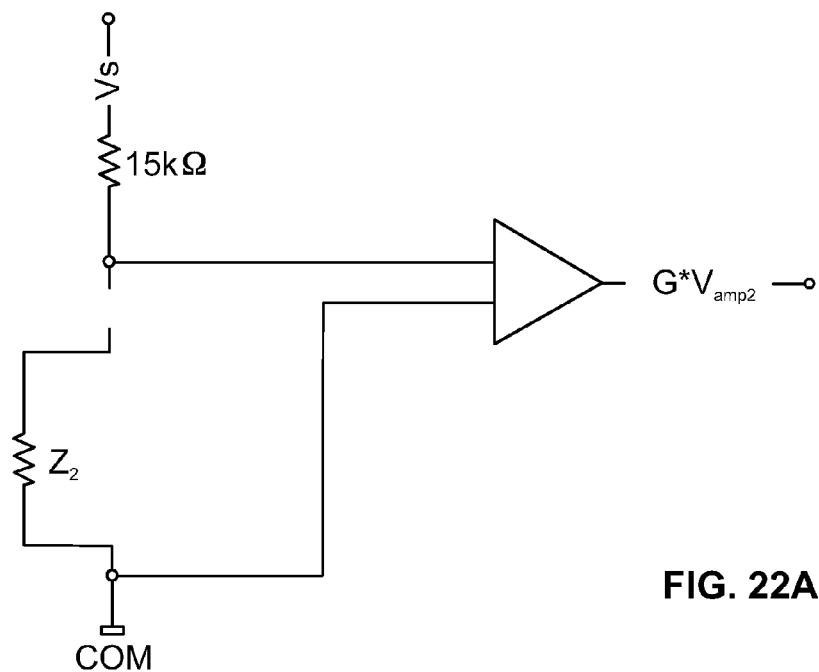
Figure 22B:
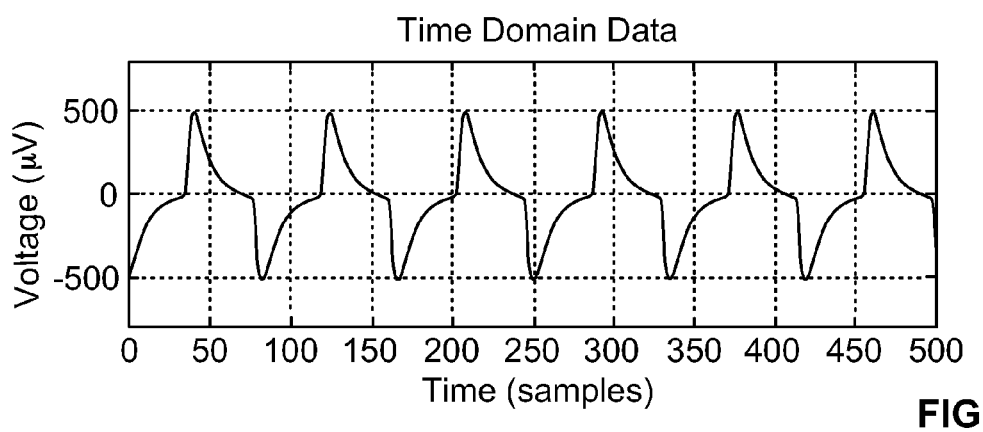
Figure 22C:
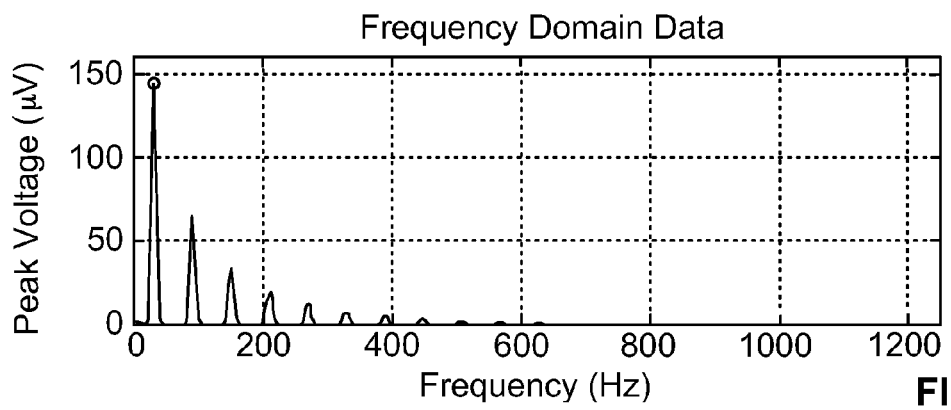
Figure 23A:
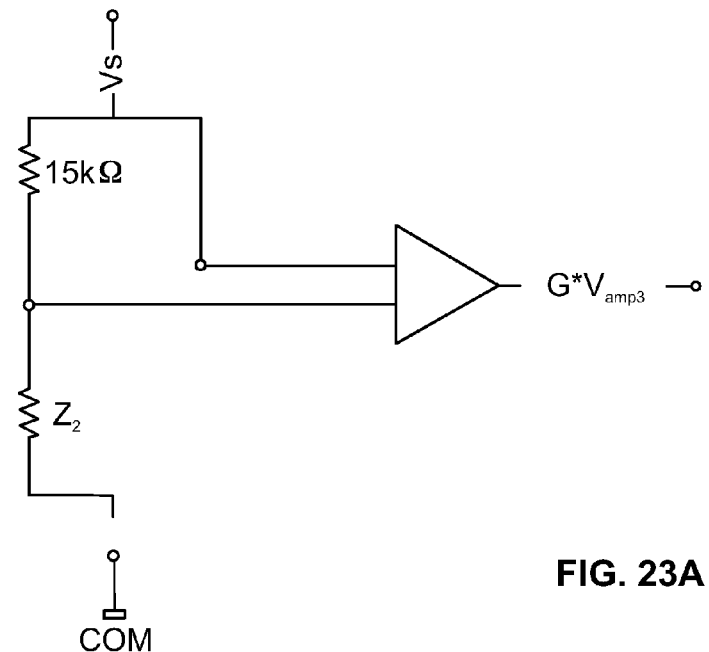
Figure 23B:
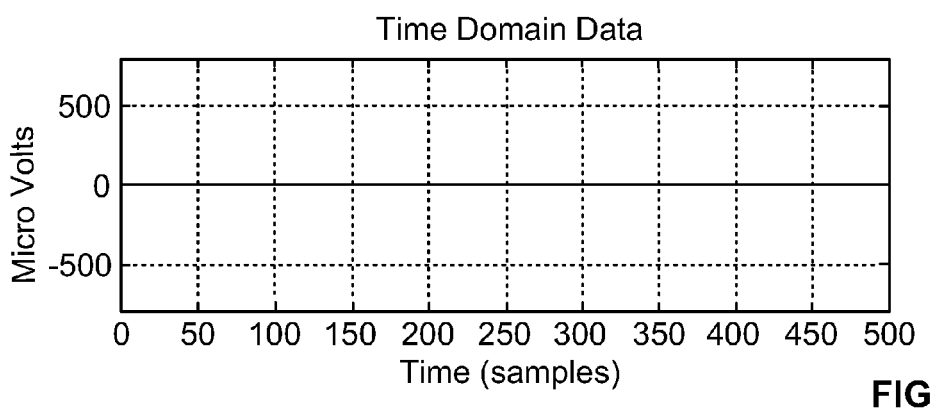
Figure 23C:
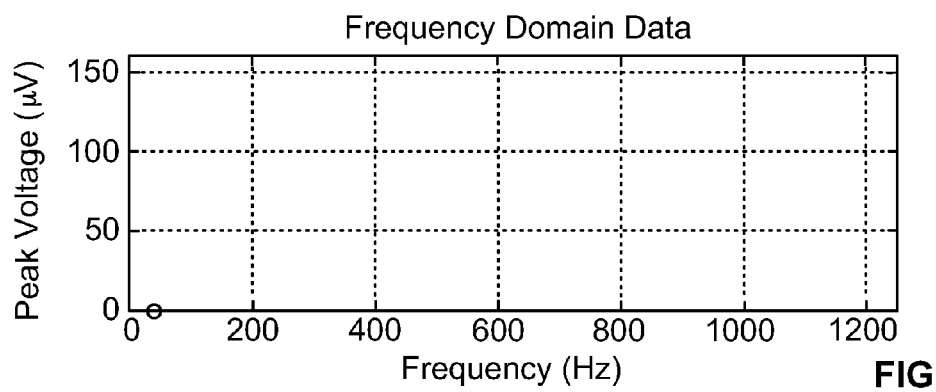

Referring now to FIGS. 21A-21C, 22A-22C and 23A-23C, it should be understood that the system 100 (FIGS. 1 and 2) is operating in a state with the $Z_1$ and $Z_c$ electrodes being disconnected from the subject (i.e., $Z_1=Z_c=\infty\Omega$). FIG. 21A shows the apparatus 200 (FIG. 2) operating in Mode 1, and FIGS. 21B and 21C show that $V_{amp1}$ is substantially similar to $V_s$ (i.e., $V_{amp1}$ theoretically should be $V_s$). FIG. 22A shows the apparatus 200 operating in Mode 2 and FIGS. 22B and 22C show that $V_{amp2}$ is substantially similar to $V_s$ (i.e., $V_{amp2}$ theoretically should be $V_s$). FIG. 23A shows the apparatus 200 operating in Mode 3, and FIGS. 23B and 23C show that $V_{amp3}$ is very close to zero (i.e., $V_{amp3}$ theoretically should be zero).

It should be appreciated that the situations of: 1) both $Z_1$ and $Z_2$ becoming disconnected; 2) both $Z_1$ and $Z_c$ becoming disconnected; and 3) all three electrodes ($Z_1$, $Z_2$, and $Z_c$) becoming disconnected from the subject provide results that are substantially similar to the foregoing-described situation of both $Z_1$ and $Z_c$ becoming disconnected (as shown in FIGS. 21A-21C, 22A-22C and 23A-23C).

Figure 24:
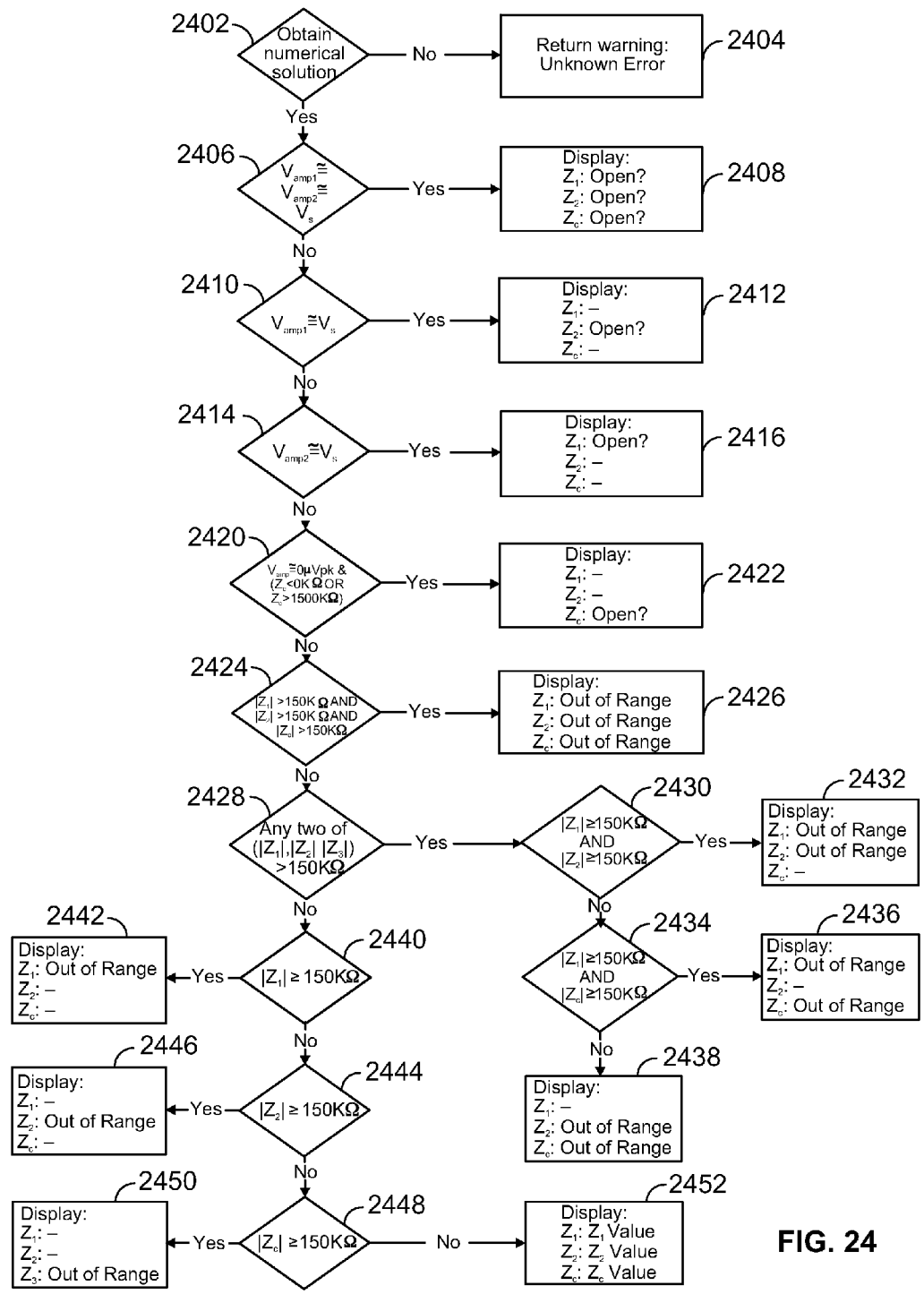
FIG. 24 illustrates a flowchart showing an example method for identifying various electrode fault conditions.

From the foregoing examples, various fault conditions can be distinguished from the corresponding values of $V_{amp1}$, $V_{amp2}$, and $V_{amp3}$ during normal non-faulted operation. An example method is shown in FIG. 24 for determining fault conditions using values of $V_{amp1}$, $V_{amp2}$, and $V_{amp3}$ and for providing an indication or warning regarding the status of the electrodes. After the method of FIG. 9 for measuring the voltage values and determining the electrode impedances is performed, the apparatus may then perform the example method of FIG. 24 to check for the existence of any fault conditions.

As shown in FIG. 24, the example method starts at step 2402 by checking the numerical solution for the electrode impedances ($Z_1$, $Z_2$, and $Z_c$). If solutions of equations 4-6 given above did not provide values for the electrode impedances, an error, warning or indication is provided at step 2404. If the values of the electrode impedances are found to be valid in step 2402, the method progresses through various decision blocks for determining whether one or more electrodes are disconnected or poorly connected. In block 2406 it is determined whether $V_{amp1}$ and $V_{amp2}$ are substantially equal and substantially similar to $V_s$. If the conditions of block 2406 are met, it is indicated in block 2408 that all three electrodes may be disconnected. However, if the conditions of block 2406 are not met, the method proceeds to block 2410. In block 2410 it is determined whether $V_{amp1}$ is substantially similar to $V_s$. If $V_{amp1}$ is substantially similar to $V_s$, it is indicated in block 2412 that the electrode corresponding to $Z_2$ is disconnected. If, in block 2410, it is determined that $V_{amp1}$ is not substantially similar to $V_s$, the method continues to block 2414. In block 2414 it is determined whether $V_{amp2}$ is substantially similar to Vs. If $V_{amp2}$ is substantially similar to Vs, it is indicated in block 2416 that the electrode corresponding to $Z_1$ is disconnected. If, in block 2414, it is determined that $V_{amp2}$ is not substantially similar to $V_s$, the method continues to block 2420.

In block 2420 it is determined if $V_{amp2}$ is about zero and if $Z_c$ is a negative value or, alternatively, very large and greater than a first predetermined value (e.g., more than 1500 kΩ). If the conditions in block 2420 are met, it is indicated in block 2422 that the electrode corresponding to $Z_c$ is disconnected. If the conditions of block 2420 are not met, the method advances to block 2424. In block 2424 it is determined if all three impedances' absolute values are large and greater than a second predetermined value (e.g., more than 150 kΩ). If the conditions of block 2424 are met, it is indicated in block 2426 that the electrode impedance values are out of range. However, if the conditions of block 2424 are not met, the method advances to block 2428.

In block 2428 it is determined if any two of the three determined impedances $Z_1$, $Z_2$, and $Z_c$ are greater than a predetermined value (e.g., more than 150 kΩ). If the condition of block 2428 is met, the method advances to block 2430. However, if the condition of block 2428 is not met, the method advances to block 2440. In block 2430, it is further determined whether the absolute value of $Z_1$ is greater than the predetermined value and whether absolute value of $Z_2$ is greater than the predetermined value. If the conditions of block 2430 are met, in block 2432 it is indicated that electrode impedance values $Z_1$ and $Z_2$ are out of range. However, if the conditions of block 2430 are not met, the method continues to block 2434. In block 2434 it is determined whether the absolute value of $Z_1$ is greater than the predetermined value and whether absolute value of $Z_c$ is greater than the predetermined value. If the conditions of block 2434 are met, in block 2436 it is indicated that electrode impedance values $Z_1$ and $Z_c$ are out of range. However, if the conditions of block 2434 are not met, the method continues to block 2438. In block 2438 it is determined (by process of elimination) that the absolute value of $Z_2$ is greater than the predetermined value and that absolute value of $Z_c$ is greater than the predetermined value. Accordingly, in block 2438 it is indicated that electrode impedance values $Z_2$ and $Z_c$ are out of range.

Turning back to block 2428, if the condition of block 2428 is not met the method advances to block 2440. In block 2440, it is determined whether the absolute value of $Z_1$ is greater than the predetermined value. If the absolute value of $Z_1$ is greater than the predetermined value, in block 2442 it is indicated that electrode impedance value $Z_1$ is out of range. However, if in block 2440 it is determined that $Z_1$ is not greater than the predetermined value, the method continues to block 2444. In block 2444, it is determined whether the absolute value of $Z_2$ is greater than the predetermined value. If the absolute value of $Z_2$ is greater than the predetermined value, in block 2446 it is indicated that electrode impedance value $Z_2$ is out of range. However, if in block 2444 it is determined that $Z_2$ is not greater than the predetermined value, the method continues to block 2448. In block 2448, it is determined whether the absolute value of $Z_c$ is greater than the predetermined value. If the absolute value of $Z_c$ is greater than the predetermined value, in block 2450 it is indicated that electrode impedance value $Z_c$ is out of range. If none of the foregoing conditions is satisfied, the electrode impedance values that were determined may be displayed in block 2452. Accordingly, the electrode impedance values may be displayed or, alternatively, an indication, warning or error message may be provided if values are determined to be out of range or if it is determined that an electrode (or more than one electrode) is disconnected.

Figure 25:
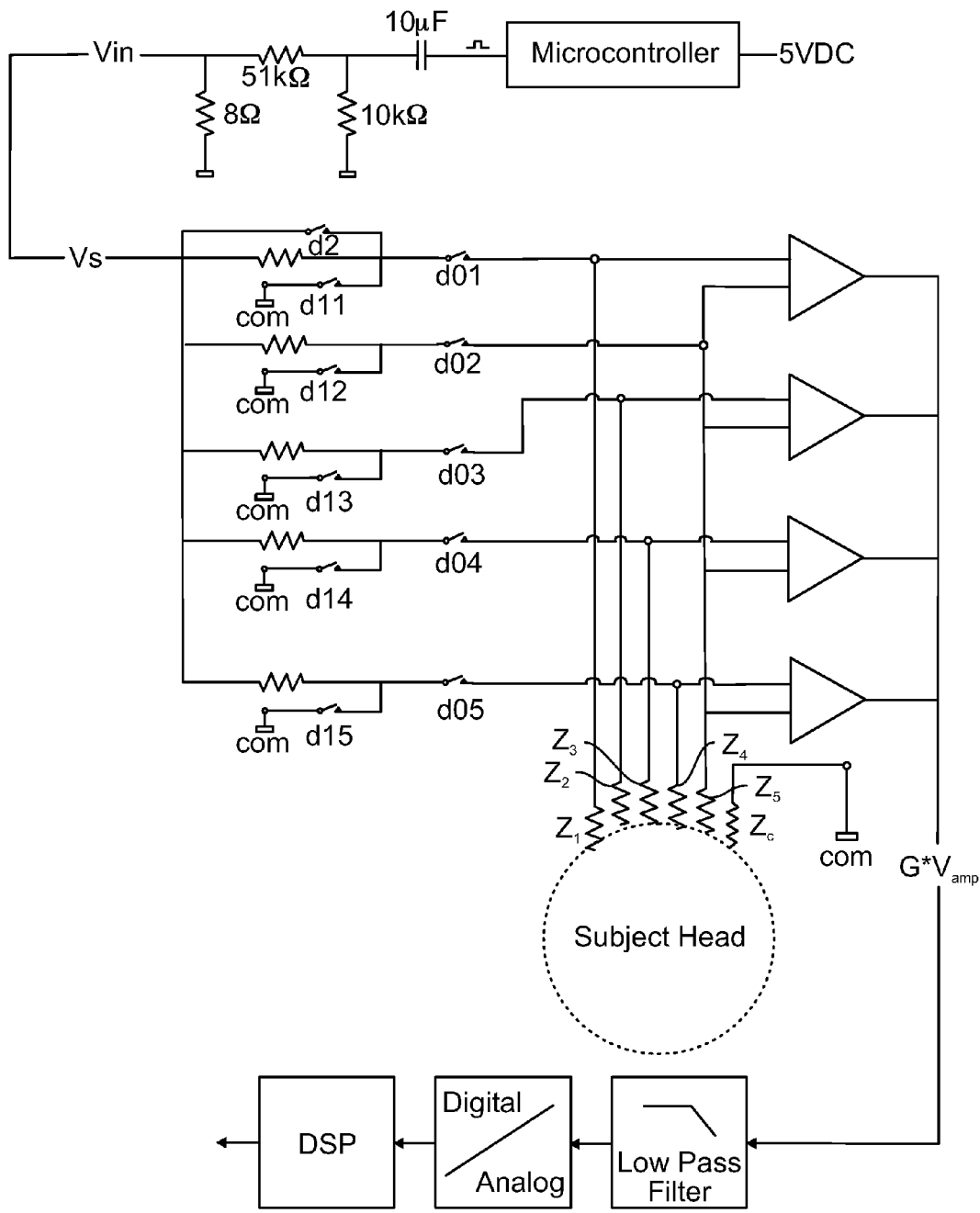
FIG. 25 illustrates a block diagram of another example apparatus according to the present invention for determining electrode impedances of a multi-channel bioelectric signal-monitoring system.

Although the illustrated and above described apparatus and method are described with respect to three electrodes $Z_1$, $Z_2$, $Z_c$, it should be appreciated that the present impedance determination apparatus and method can be used on systems using fewer or additional electrodes. For example, FIG. 25 shows an example apparatus that is configured to determine the impedance of six electrodes. Indeed, the present apparatus and method may be adapted to multiple channels and numbers of electrodes.

It should be appreciated that the present apparatus and method may be configured or adapted in various ways. In one example embodiment, apparatuses and methods according to the present invention may perform a step of dropping/decreasing the amplifier gain (e.g., by a factor of 10) during the impedance checking operation. As can be appreciated, decreasing the amplifier gain allows use of a large output signal to obtain more accurate measurements without saturating the amplifier 140. Accordingly, the present apparatus 200, particularly the controller 250, may communicate with the system 100, particularly the amplifier 140, for adjusting the amplifier gain.

In another example embodiment, apparatuses and methods according to the present invention may perform a step of decreasing the settling time of an amplifier. As previously described with reference to FIG. 10A, there is a brief transient in the data following the original event (e.g., mode switching) that causes an amplifier's output to become temporarily unreliable/unusable. As known in the art, bio-signal amplifiers include various gain stages and filters, e.g. a high-pass filter (HPF) with a large time constant (i.e. very low cutoff frequency such as 0.3 Hz) because using a large time constant in the HPF preserves lower frequency components in the acquired data while still eliminating DC. It has been observed that amplifier 140 settling time is directly related to the settling time of the HPF as opposed to the individual gain stages.

Accordingly, the apparatus 200 can help the amplifier 140 recover faster as the controller 250 switches between the impedance checking modes by reducing the time constant of the HPF by, for example, changing a resistance value of the HPF. In an example, the resistance of the HPF may be reduced by electrically connecting (e.g., using a controlled, switched resistance that is selectively connected relative to an output of a saturation-detection module) to an additional resistance in parallel with a resistance of the HPF. In this way, the apparatus 200 may make a high-speed sequence of measurements using fast amplifier recovery. The HPF can, optionally, be kept in this fast recovery state during impedance measurement, as long as the additional attenuation to Vs is taken into account when computing $Z_1$, $Z_2$, and $Z_c$. That is, we can expect $V_s$ to be smaller when the HPF time constant is reduced.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Various embodiments of this invention are described herein. However, it should be understood that the illustrated embodiments are exemplary only and should not be taken as limiting the scope of the invention.

What is claimed is:

1. An apparatus for determining individual electrode impedance values for all electrodes of a bioelectric signal-monitoring system including a differential amplifier and only two signal electrodes which connect between a subject and inputs of the amplifier and a ground or common electrode which connects between the subject and a common or ground point in the system, without interruption of any of said electrode connections, the apparatus comprising:
 a signal source outputting a voltage signal;
 a first switching arrangement, including inputs electrically connected with the signal source through known impedances for receiving the voltage signal, outputs electrically connected with the signal electrodes, and switches between the inputs and the outputs; and
 a second switching arrangement, including inputs electrically connected with the signal electrodes, outputs electrically connected with the ground or common point in the system, and switches between the inputs and the outputs; and
 a controller in communication with the first and second switching arrangements for establishing a plurality of signal paths, wherein each signal path corresponds to a predetermined mathematical equation expressing an electrode impedance in terms of an equivalent signal path impedance and a voltage output of the differential amplifier; and
 the controller further comprising an algorithm for solving a plurality of mathematical equations corresponding to the plurality of signal paths to determine the electrode impedances.

2. The apparatus of claim 1 wherein the signal source is configured to output a bipolar voltage signal.

3. The apparatus of claim 2 wherein the bipolar voltage signal has a repetition rate in the range of 20 Hz, 50% duty cycle, and 0V of DC offset.

4. The apparatus of claim 1 wherein the function of calculating the electrode impedances, relative to voltage outputs of the amplifier for each signal path, is embodied in a processor, different from the controller.

5. The apparatus of claim 1 wherein the switches are field effect transistors.

6. The apparatus of claim 1 wherein the controller is further configured to output a signal for generating at least one of an indication of the electrode impedances, and an indication providing a warning or alarm of an electrode fault condition.

7. The apparatus of claim 1 wherein the signal source is integral with the controller.

8. The apparatus of claim 1 wherein at least one distinct signal path is associated with each electrode.

9. The apparatus of claim 1 wherein the plurality of mathematical equations are predetermined or solvable numerically.

10. The apparatus of claim 1 wherein the switches in the first switching arrangement are permanently conducting when configured as a stand-alone apparatus.

11. The apparatus of claim 1 wherein the controller converts the output voltages from the differential amplifier from the time domain to the frequency domain.

12. The apparatus of claim 11 wherein the controller further determines a peak value of the frequency domain data in a predetermined frequency range.

13. The apparatus of claim 12 wherein each signal path is expressed as a mathematical equation defining an electrode impedance in terms of an equivalent signal path impedance and a corresponding peak value.

14. The apparatus of claim 13 wherein the controller comprises an algorithm for solving the plurality of mathematical equations to determine the individual electrode impedance values.

15. The apparatus of claim 1 wherein at least one electrode fault condition is determined by comparing the computed skin-to-electrode impedances with predetermined impedance values, the apparatus further comprising an indicator, wherein:
    if an electrode fault condition is determined, the indicator is a warning or alarm; and
    if an electrode fault condition is not determined, the indicator is the skin-to-electrode impedances.

16. The apparatus of claim 15 wherein the warning or alarm indicator includes an identification as to which one or more of the electrodes caused the fault condition.

17. The apparatus of claim 1 wherein the controller comprises:
    an algorithm for multiplying the output voltage data from the differential amplifier by a window function; and
    an algorithm for performing a Fast Fourier Transform on windowed data from the algorithm for multiplying.

18. An apparatus for determining individual electrode impedance values for all electrodes of a bioelectric signal-monitoring system including a differential or referential amplifier and two or more signal electrodes, wherein the signal electrodes may include one or more reference electrodes, which connect between a subject and the inputs of the amplifier and a ground or common electrode which connects between the subject and a common or ground point in the system, without interruption of any of said electrode connections, the apparatus comprising:
    a signal source outputting a voltage signal;
    a first switching arrangement, including inputs electrically connected with the signal source through known impedances for receiving the voltage signal, outputs electrically connected with the signal electrodes, and switches between the inputs and the outputs; and
    a second switching arrangement, including inputs electrically connected with the signal electrodes, outputs electrically connected with the ground or common point in the system, and switches between the inputs and the outputs; and
    a controller in communication with the first and second switching arrangements for establishing a plurality of signal paths, wherein each signal path corresponds to a predetermined mathematical equation expressing an electrode impedance in terms of an equivalent signal path impedance and a voltage output of the amplifier; and
    the controller further comprising an algorithm for solving a plurality of mathematical equations corresponding to the plurality of signal paths to determine the electrode impedances.

19. The apparatus of claim 18 wherein the signal source is configured to output a bipolar voltage signal.

20. The apparatus of claim 19 wherein the bipolar voltage signal has a repetition rate in the range of 20 Hz, 50% duty cycle, and 0V of DC offset.

21. The apparatus of claim 18 wherein the function of calculating the electrode impedances, relative to voltage outputs of the amplifier for each signal path, is embodied in a processor, different from the controller.

22. The apparatus of claim 18 wherein the switches are field effect transistors.

23. The apparatus of claim 18 wherein the controller is further configured to output a signal for generating at least one of an indication of the electrode impedances, and an indication providing a warning or alarm of an electrode fault condition.

24. The apparatus of claim 18 wherein the signal source is integral with the controller.

25. The apparatus of claim 18 wherein at least one distinct signal path is associated with each electrode.

26. The apparatus of claim 18 wherein the plurality of mathematical equations are predetermined or solvable numerically.

27. The apparatus of claim 18 wherein the switches in the first switching arrangement are permanently conducting when configured as a stand-alone apparatus.

28. The apparatus of claim 18 wherein the controller converts the output voltages from the amplifier from the time domain to the frequency domain.

29. The apparatus of claim 28 wherein the controller further determines a peak value of the frequency domain data in a predetermined frequency range.

30. The apparatus of claim 29 wherein each signal path is expressed as a mathematical equation defining an electrode impedance in terms of an equivalent signal path impedance and a corresponding peak value.

31. The apparatus of claim 30 wherein the controller comprises an algorithm for solving the plurality of mathematical equations to determine the individual electrode impedance values.

32. The apparatus of claim 18 wherein at least one electrode fault condition is determined by comparing the computed skin-to-electrode impedances with predetermined impedance values, the apparatus further comprising an indicator, wherein:
- if an electrode fault condition is determined, the indicator is a warning or alarm; and
- if an electrode fault condition is not determined, the indicator is the skin-to-electrode impedances.

33. The apparatus of claim 32 wherein the warning or alarm indicator includes an identification as to which one or more of the electrodes caused the fault condition.

34. The apparatus of claim 18 wherein the controller comprises:
- an algorithm for multiplying the output voltage data from the amplifier by a window function; and
- an algorithm for performing a Fast Fourier Transform on windowed data from the algorithm for multiplying.

35. A method for determining skin-to-electrode impedances of a bioelectric signal-monitoring system including an amplifier and electrodes attached to the skin of a subject, the method comprising:
- electrically connecting an impedance-determining apparatus with inputs of the amplifier to which the electrodes are connected for monitoring bioelectric signals, the impedance-determining apparatus including a voltage source, a switching arrangement, and a plurality of resistors having known impedances, each comprising an input connected to the voltage source and an output switchably connected to a ground or common reference point in the system, and also switchably connected to at least one of the electrodes;
- measuring output voltages of the amplifier during operation of the impedance-determining apparatus, operation of the impedance-determining apparatus comprising establishing a plurality of signal paths between the voltage source, at least one of the plurality of resistors, and the inputs of the amplifier;
- and calculating a skin-to-electrode impedance for each signal path of the quantity relative to output voltages from the measuring step.

36. A method for determining individual electrode impedance values for all electrodes of a bioelectric signal-monitoring system including a differential amplifier and only two signal electrodes which connect between a subject and inputs of the amplifier and a ground or common electrode which connects between the subject and a common or ground point in the system, without a interruption of any of said electrode connections, the method comprising:
- outputting a voltage signal by a signal source;
- receiving the voltage signal by inputs of a first switching arrangement electrically connected with the signal source through known impedances, the first switching arrangement having outputs electrically connected with the signal electrodes, and switches between the inputs and the outputs;
- providing a second switching arrangement, including inputs electrically connected with the signal electrodes, outputs electrically connected with the ground or common point in the system, and switches between the inputs and the outputs; and
- establishing a plurality of signal paths with a controller having a processor in communication with the first and second switching arrangements, wherein each signal path corresponds to a predetermined mathematical equation expressing an electrode impedance in terms of an equivalent signal path impedance and a voltage output of the differential amplifier; and
- solving, with the controller, a plurality of mathematical equations corresponding to the plurality of signal paths to determine the electrode impedances.

37. An apparatus for determining electrode impedance values for all electrodes of a bioelectric signal-monitoring system including a amplifier and a plurality of electrodes which connect between a subject and inputs of the amplifier and a ground or common electrode, without interruption of any of said electrode connections, the apparatus comprising:
- a voltage source outputting a voltage signal;
- a plurality of resistors having known impedances, each comprising: an input connected to the voltage source; and an output switchably connected to a ground or common reference point in the system, and also switchably connected to at least one of the electrodes;
- a switching arrangement including an input electrically connected with the voltage source for receiving the voltage signal, an output electrically connected with the electrodes and the input of the amplifier, and switches between the input and the output that are connected to the plurality of resistors; and
- a controller in communication with the switches for opening and closing the switches to establish signal paths between the voltage source, at least one of the plurality of resistors, and the output, the controller calculating the electrode impedances relative to voltage outputs of the amplifier for each signal path.

* * * * *